(12) United States Patent
Loyau et al.

(10) Patent No.: US 9,999,679 B2
(45) Date of Patent: Jun. 19, 2018

(54) AMINOFUCOIDAN AS A VECTOR FOR FIBRINOLYSIS IN THROMBOTIC DISEASES

(71) Applicants: INSTITUT NATIONAL DE LA SANTE ET DE LA RECHERCHE MEDICALE, Paris (FR); UNIVERSITE PARIS XIII PARIS NORD, Villetaneuse (FR); UNIVERSITE PARIS DIDEROT—PARIS 7, Paris (FR)

(72) Inventors: Stephane Loyau, Paris (FR); Martine Jandrot-Perrus, Paris (FR); Didier Letourneur, Paris (FR); Frederic Chaubet, Villetaneuse (FR); Benoit Ho-Tin-Noe, Paris (FR); Murielle Maire, Villetaneuse (FR); Jean-Baptiste Michel, Paris (FR)

(73) Assignees: INSTITUT NATIONAL DE LA SANTE ET DE LA RECHERCHE MEDICALE, Paris (FR); UNIVERSITE PARIS XIII PARIS NORD, Villetaneuse (FR); UNIVERSITE PARIS DIDEROT—PARIS 7, Paris (FR)

( * ) Notice: Subject to any disclaimer, the term of this patent is extended or adjusted under 35 U.S.C. 154(b) by 268 days.

(21) Appl. No.: 14/778,259

(22) PCT Filed: Mar. 21, 2014

(86) PCT No.: PCT/IB2014/060039
§ 371 (c)(1),
(2) Date: Sep. 18, 2015

(87) PCT Pub. No.: WO2014/147597
PCT Pub. Date: Sep. 25, 2014

(65) Prior Publication Data
US 2016/0279249 A1    Sep. 29, 2016

(30) Foreign Application Priority Data

Mar. 21, 2013 (EP) .................................... 13305340

(51) Int. Cl.
| | | |
|---|---|---|
| A01N 43/04 | (2006.01) |
| A61K 31/715 | (2006.01) |
| A61K 47/48 | (2006.01) |
| A61K 38/49 | (2006.01) |
| A61K 45/06 | (2006.01) |
| A61K 31/737 | (2006.01) |
| C08B 37/00 | (2006.01) |
| A61K 31/716 | (2006.01) |

(52) U.S. Cl.
CPC ........ *A61K 47/4823* (2013.01); *A61K 31/737* (2013.01); *A61K 38/49* (2013.01); *A61K 45/06* (2013.01); *A61K 47/48038* (2013.01); *A61K 47/48046* (2013.01); *A61K 47/48215* (2013.01); *C08B 37/0006* (2013.01); *C12Y 304/21068* (2013.01); *A61K 31/715* (2013.01); *A61K 31/716* (2013.01)

(58) Field of Classification Search
None
See application file for complete search history.

(56) References Cited

U.S. PATENT DOCUMENTS

2012/0183475 A1    7/2012    Michel et al.

FOREIGN PATENT DOCUMENTS

| WO | 2007127298 A2 | 11/2007 |
| WO | 2010/049611 A1 | 5/2010 |
| WO | 2010/116209 A1 | 10/2010 |
| WO | 2012/102555 A2 | 8/2012 |

OTHER PUBLICATIONS

Suzana et al., "Synthesis of amine-functionalized heparin oligosaccharides for tge investigation of carbohydrate-protein interactions in microtiter plates", Organic and Biomolecular Chemistry, Jan. 1, 2012, p. 2146, vol. 10, No. 10.
Soeda et al., "Preparation of aminated fucoidan and its evaluation as an antithrombotic and antilipemic agent", Biological and Pharmaceutical Bulletin, 1994, pp. 788-784, vol. 17, No. 6.
Carranza et al., "Effect of oversulfated chondroitin-6-sulfate or oversulfated fucoidan in the activation of glutamic plasminogen by tissue plasminogen activator: role of lysine and cyanogen bromide-fibrinogen", Blood Coagulation & Fibrinolysis: An International Journal in Haemostasis and Thrombosis, Jan. 2008, vol. 19, No. 1.
Madureira et al., "The role of the annexin A2 heterotetramer in vascular fibrinolysis", Blood, Nov. 3, 2011, pp. 4789-4797, vol. 118, No. 18.
Wang et al., "In-vitro anticoagulant activity of fucoidan derivatives from brown seaweed", Chinese Journal of Oceanology and Limnology, May 15, 2011, pp. 679-685, vol. 29, No. 3.
Soeda et al., "Aminated fucoidan promotes the invasion of 3 LL cells through reconstituted basement membrane: Its possible mechanism of action", Cancer Letters 85 (1994) 133-138.
Wang et al., "Synthesized phosphorylated and aminated derivatives of fucoidan and their potential antioxidant activity in vitro", International Journal of Biological Macromolecules 44 (2009) 170-174.

*Primary Examiner* — Patrick T Lewis
(74) *Attorney, Agent, or Firm* — Whitham, Curtis & Cook, P.C.

(57) ABSTRACT

The invention relates to a vector targeting thrombus, having t-PA binding property consisting of a thrombus targeting fucoidan moiety, which is covalently linked to one or more t-PA binding amino groups by the reducing end of the said fucoidan moiety.

19 Claims, 2 Drawing Sheets

SEQUENCE LISTING

```
<160> NUMBER OF SEQ ID NOS: 1

<210> SEQ ID NO 1
<211> LENGTH: 562
<212> TYPE: PRT
<213> ORGANISM: Homo sapiens
<220> FEATURE:
<221> NAME/KEY: SOURCE
<222> LOCATION: 1..562
<223> OTHER INFORMATION: /mol_type="protein"
      /organism="Homo sapiens"

<400> SEQUENCE: 1

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240
```

```
Ser Met Ile Leu Ile Gly Lys Val Tyr Thr Ala Gln Asn Pro Ser Ala
            245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
            275                 280                 285

Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
            355                 360                 365

Thr Val Ile Leu Gly Arg Thr Tyr Arg Val Val Pro Gly Glu Glu Glu
    370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
            435                 440                 445

Tyr Gly Lys His Glu Ala Leu Ser Pro Phe Tyr Ser Glu Arg Leu Lys
    450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
            500                 505                 510

Ser Gly Gly Pro Leu Val Cys Leu Asn Asp Gly Arg Met Thr Leu Val
            515                 520                 525

Gly Ile Ile Ser Trp Gly Leu Gly Cys Gly Gln Lys Asp Val Pro Gly
    530                 535                 540

Val Tyr Thr Lys Val Thr Asn Tyr Leu Asp Trp Ile Arg Asp Asn Met
545                 550                 555                 560

Arg Pro
```

US 9,999,679 B2

AMINOFUCOIDAN AS A VECTOR FOR FIBRINOLYSIS IN THROMBOTIC DISEASES

FIELD OF THE INVENTION

The invention relates to improved systems and molecular strategies for the prevention and treatment of acute vascular thrombotic diseases.

More particularly, the invention relates to intravenous recombinant tissue plasminogen activator-induced fibrinolysis using vectorization of tissue plasminogen activator (also referred herein as t-PA) to thrombus by a chimeric bipolar molecule including an amine-containing moiety that binds to tissue plasminogen activator, and a fucoidan moiety that binds to thrombus performing a vecteur system able both to protect intravenously-injected t-PA during its plasma transport and to vectorize it to the intravascular thrombus.

Thus, according to one of its aspects, the invention relates to a vector having t-PA binding property consisting of a fucoidan moiety, which is aminated by a covalent linkage between the reducing end of the said fucoidan moiety and a chemical group comprising one or more amino groups.

According to another of its aspects, the invention relates to a vectorized t-PA and/or pharmaceutical compositions comprising it, as well as methods to prepare said thrombus-vectorized t-PA or pharmaceutical compositions.

BACKGROUND OF THE INVENTION

Hemostasis can be defined as an essential homeostatic system leading to the formation of a hemostatic clot. Hemostatis has to be finely tuned in order to avoid the risk of bleeding, or haemorrhage, and the appearance of pathologic obstructive blood clots, also referred herein as thrombosis. Acute thrombotic events remain the main cause of mortality and morbidity in western countries.

The formation of a clot results from the coordinated activation of the coagulation cascade and of platelets. This is an amplified process with activating platelets supporting the assembly of coagulation enzymatic complexes and the final enzyme of the coagulation, thrombin being a potent activator of platelets. The final product is composed of aggregates of platelets expressing specific sites at their surface and of polymerized fibrin fibres. The respective role of coagulation and platelets may vary according to the vascular bed and rheological conditions, platelets and fibrin being more predominant in arterial and venous thrombi respectively.

For a better comprehension of coagulation as a dynamic process, the man skilled in the art may also refer for complementary information to Kottke-Marchant & Lefkowitz (KOTTKE-MARCHANT & LEFKOWITZ, 2008, Chapter 1—Coagulation Pathway and Physiology. An Algorithmic Approach to Hemostasis Testing).

When a hemostatic clot is formed, one has to consider additional biological mechanisms that provoke secondary clot resorbtion, allowing tissue reparation (healing). Those secondary mechanisms may be commonly referred as the clot removal system, or «fibrinolysis».

One has to consider that a clot is in permanent equilibrium between building and destruction. When a thrombotic clot is formed in an artery of vein, spontaneous resorbtion of the clot is too delayed to be efficient to protect downstream tissue from irreversible ischemia. Thus two strategies are currently used to treat thrombosis: (i) to limit the incremental formation of the clot by antiplatelet and anticoagulant drugs and (ii), to enhance clot destruction by inducing fibrinolysis.

The invention refers to this second strategy.

The fibrinolytic pathway is composed of both activators and inhibitors. Thus, an «activator» of the fibrinolytic pathway may have the ability to provoke lysis of fibrin, whereas an «inhibitor» of the fibrinolytic pathway may have the opposite effect.

During its formation, the clot exposes the elements required for its resorbtion: fibrin exposes binding sites for the circulating zymogen plasminogen and its activator, the tissue-type plasminogen activator (t-PA). The formation of a ternary complex in which fibrin, plasminogen and t-PA are associated, ensure the efficacy of the fibrinolysis and prevents its extension to the blood stream (fibrinogenolysis). Fibrin-bound plasminogen is cleaved at Arg-561-Val562 by its activator t-PA, generating the disulfide bond linked two chain protease plasmin.

It is well known that t-PA and plasmin bind to cationic residues, mainly amine ($NH_2$) groups of lysine residues expressed on the fibrin network (Lijnen et al., 2001, Elements of the fibrinolytic system. Ann N Y Acad Sci, 936, 226-236).

Furthermore, plasminogen binds with a high affinity to carboxy terminal lysines (Lys). Plasmin cleavage of fibrin exposes new carboxy-terminal Lys, leading to more plasminogen binding sites and more plasmin formed (amplification process). In contrast, TAFI (Thrombin-Activable Fibrinolysis Inhibitor), a carboxypeptidase, removes the carboxy terminal Lys, preventing binding of plasminogen and inhibiting fibrinolysis. The t-PA also binds to side chain free amine.

Lysine mimetics, such as □-amino caproic acid or tranexamic acid (Royston, 1995, Blood-sparing drugs: Aprotinin, tranexamic acid, and epsilon-aminocaproic acid, Int Anesthesiol Clin), displace plasminogen from C-terminal lysine residues, thus limiting fibrinolysis. On the other hand, amine-bound t-PA is protected from inhibition by serpins, mainly the plasminogen activator inhibitor (PAI-1) also known as endothelial plasminogen activator inhibitor or as serpin E1.

Acute non-interventional treatment remains mainly the intravenous injection of recombinant tissue plasminogen activator, also referred herein as rt-PA (Altéplase, Actilyse® or Tenecteplase, Metalyse®, Boehringer Ingelheim). For example international guidelines recommend the earliest IV injection of recombinant t-PA in acute stroke (group IST et al., 2012, The benefits and harms of intravenous thrombolysis with recombinant tissue plasminogen activator within 6 h of acute ischaemic stroke (the third international stroke trial [ist-3]): A randomised controlled trial, Lancet). But the efficacy of recombinant t-PA peripheral injection is limited to 10% due to:

dilution of the potent compound in the whole blood,
inhibition of recombinant t-PA by circulating chelators such as PAI-1 during its plasma traffic,
low initial level of rt-PA binding to the thrombus.
increased risk of hemorrhage for high doses and delayed injection.

Furthermore, although thrombolytic effects of t-PA are beneficial, its neurotoxicity, at the required high dose ranges that are presently used, is problematic.

To tentatively protect rt-PA from plasma inhibitors, it is conditioned in the presence of Arg (Alteplase formulation). The protective effect of amine residues has also been exploited with the use of annexin 2 as a chaperone. Indeed, the colocalisation of plasminogen and t-PA at the cell surface allows cells to play a regulatory role on fibrinolysis. The annexin2-S100A10 complex provides such a platform for the activation of plasminogen thanks to the presentation of a C-terminal Lys in the correct three dimensional orientation for recognition of t-PA and plasminogen (Madureira et al., 2011 The role of the annexin A2 heterotetramer in vascular fibrinolysis, Blood), In this context, annexin A2 has been proposed with success, as a chaperone for IV injection of t-PA (Zhu et al., 2010, Annexin 2 combined with low-dose t-PA improves thrombolytic therapy in a rat model of focal embolic stroke, J Cereb Blood Flow Metab). Limitations to this strategy are the absence of t-PA vectorization and the fact that annexin A2 is a recombinant protein highly expensive to produce.

There is a general need for improved treatments related to acute vascular thrombotic diseases. There is thus an urgent need for new forms of t-PA, or t-PA-derived active compounds more therapeutically effective at amounts of t-PA lower than those currently administered, so as to at least temperate the toxic side effects of this active ingredient.

Thus, protection of t-PA during its plasma circulation and its efficient vectorization to the thrombus represent an important challenge.

SUMMARY OF THE INVENTION

The present invention relates to a compound having the ability to bind both to t-PA and thrombus and which is able to vectorize therapeutic t-PA at its biological target.

This invention concerns such a vector compound, which comprises a thrombus-targeting fucoidan moiety covalently bound to an amine containing group with t-PA binding and t-PA protecting properties.

The thrombus-binding property of the fucoidan moiety is used to target the therapeutic compound to the clot.

Thus, the present invention pertains to a vector having t-PA binding property consisting of a fucoidan moiety, which is aminated by a covalent linkage between the reducing end of the said fucoidan moiety and a chemical group comprising one or more amino groups (—$NH_2$), such as primary amine groups or guanidine groups.

In certain embodiments, the said vector is a compound of formula (I):

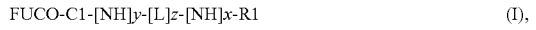

FUCO-C1-[NH]y-[L]z-[NH]x-R1        (I), wherein

"FUCO" means a fucoidan moiety, optionally containing one or more primary amine groups covalently linked to the fucoidan chain, x, y and z are independent integers meaning 0 or 1, C1 is the carbon atom at position 1 of the saccharide unit located at the reducing end of the fucoidan moiety, L is a linker, and R1 is a chemical group comprising one or more amino groups, or consisting in one amino group, L and R1 are independent and may be equal or different.

In some embodiments, the said vector is a compound of formula (I), wherein:

R1 is a chemical group comprising or consisting in a primary-amine ended, linear or branched hydrocarbon chain; an aminoacid; a polyaminoacid; and/or a chemical group selected in the list comprising, or consisting in: lysine, polylysine, arginine, polyarginine, ornithine, polyornithine, γ-aminobutyric acid, polyamines, polyetheramines, or any other chemical group comprising a guanidine group or a primary amine, wherein:

the said chemical group is optionally interrupted by one or more non aromatic hydrocarbon ring(s) having 5 or 6 carbon atoms, and preferably not more than one non aromatic hydrocarbon ring having 5 or 6 carbon atoms, the said chemical group is optionally interrupted by one or more heteroatoms, the said chemical group is optionally containing one or more amide groups and/or one or more ester groups, in particular one or more amide groups, the said chemical group is optionally substituted by one or more amine groups, the said chemical group is optionally interrupted and/or substituted by one or more group(s), identical or different, and selected from: (a) a linear or branched hydrocarbon chain, (b) an aminoacid or a polyaminoacid (c) a polyamine or a polyetheramine, (d) a γ-aminobutyric acid (e) a guanidine group and (f) a primary amine.

In some embodiments of the said vector, the fucoidan moiety has an average molecular weight which is lower than 100 000 Da, preferably lower than 20 000 Da, and in particular ranging from 2000 Da to 15 000 Da.

This invention also relates to a vectorized t-PA comprising complexes of a vector as defined above with t-PA.

In some embodiments, the said vectorized t-PA a molar ratio of vector to t-PA ranging from 40:1 to 1:1; preferably from 20:1 to 3:1, and most preferably from 15:1 to 5:1.

This invention also concerns a method for preparing a vectorized t-PA comprising the steps of:

a) providing a vector as defined above, b) providing t-PA, and c) bringing into contact the vector provided at step a) with the t-PA provided at step b), so as to obtain complexes between the said vector and t-PA.

It also pertains to a kit comprising:

a first container comprising a vector as defined above, and a second container comprising t-PA.

The present invention also pertains to a pharmaceutical composition comprising complexes of a vector as defined above with t-PA, as well as to the therapeutic uses of the said pharmaceutical composition.

Platelet-rich clots were incubated with rt-PA (control, first column), or rt-PA complexed to aminofucoidans (second, third and fourth column) or non-aminated fucoidan (column 7) or fucoidan alone (column 6). Fibrin lysis was measured and is expressed as a percentage in the y axis. The median value is indicated with a horizontal bar (n=3 per condition). Di-lys and Tri lys (second and third column) stand respectively for di-lysine and tri-lysine. Ac-Tran (fourth column) stands for tranexamic acid and DETA (fifth column) for diethylenetriamine.

Figure 2:
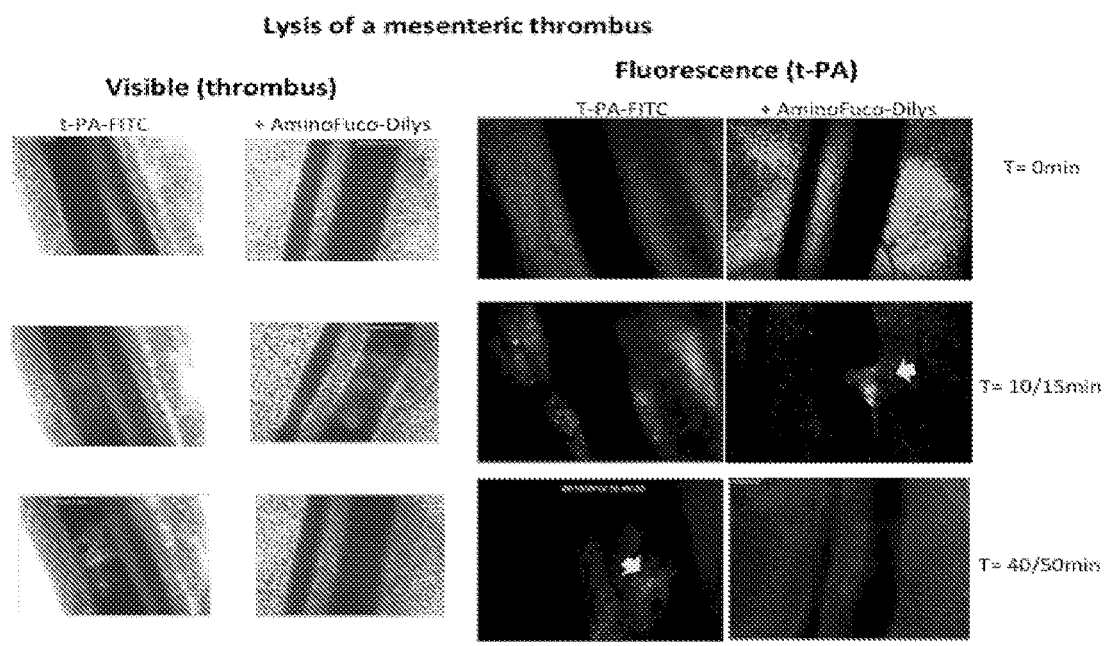

FIG. 2: In vivo lysis of mesenteric thrombi by vectorized t-PA in mice.

At time 0 thrombosis of mesenteric vessels was induced by exposure to $FeCl_3$ and occurred at T=10/15 minutes. Thrombolysis was induced by r-tPA (control) or aminofucoidan-coupled rtPA. Lysis was observed only when induced by aminofucoidan in 40 to 50 min. Mesenteric exposed vessels are observed both with visible light (left column) and fluorescence (right column) using t-PA-FITC.

DETAILED DESCRIPTION OF THE INVENTION

Fucoidan, referring to a type of sulfated polysaccharide (polyanion) mainly derived from brown seaweed, is a naturally occurring mimic of Sialyl-Lewis$^X$ (Li et al., 2008, Fucoidan: Structure and bioactivity, Molecules).

Sialyl Lewis$^X$, also known as sialyl Le$^X$ and SLe$^X$, is a tetrasaccharide carbohydrate that can be attached to O-glycans or N-glycans on the surface of cells, and that is important for cell-cell recognition.

It is able to bind platelet P-selectin (Bachelet, 2009, Affinity of low molecular weight fucoidan for P-selectin triggers its binding to activated human platelets, Biochim Biophys Acta) and intraluminal thrombus in vivo (Rouzet et al., 2011, Radiolabeled fucoidan as a P-selectin targeting agent for in vivo imaging of platelet-rich thrombus and endothelial activation, J Nucl Med).

It is now shown that an aminofucoidan can act as a vectorizing agent for tissue plasminogen activator to intraluminal vascular clot. In particular, it is shown that an aminofucoidan can act as vector for the prevention and/or treatment of pathologies associated with the appearance of intraluminal thrombus in a subject and/or in thrombotic diseases.

According to the invention, a «vector» or «vectorizing agent» refers to a biological agent, comprising a fucoidan or a fucoidan moiety, as a vehicle to carry a molecule, in particular a protein, to a blood clot.

The «subject», or «biological target», may be any biological entity that can produce and/or contains selectins. For example, the biological target may be a cell, a biological fluid or a biological tissue. The biological target may originate from a living subject (e.g., it may be obtained by drawing blood, or by biopsy) or a deceased subject (e.g., it may be obtained at autopsy). The subject may be human or another mammal. In certain preferred embodiments, the biological target originates from a patient suspected of having a clinical condition associated with the appearance of an intravascular thrombus. In particular, said subject may suffer from a chronic or acute thrombotic disease or thrombotic disorder.

According to the invention, the term «activator of plasminogen», or t-PA, also encompasses native and recombinant t-PA, for instance a two-chain t-PA or a single-chain recombinant t-PA. In humans, t-PA is a protein of SEQ ID NO1, or as described in Harris et al. (Harris et al., 1986, Cloning of cDNA coding for human tissue-type plasminogen activator and its expression in *Escherichia coli*, Mol. Biol. Med. 3 (3), 279-292).

According to the invention, fucoidans refer to a type of polysaccharide, which contains substantial percentages of L-fucose and sulfate ester groups, mainly derived from brown seaweed and some other marine invertebrates. Said fucoidans can be obtained by various methods known in the art, which will be developed further below. For a more complete review on the structure and bioactivity of fucoidans, the man skilled in the art may refer to Li et al. (Li et al., 2008, Fucoidan: Structure and Bioactivity, Molecules).

The terms «fucoidan», «fucoidan moiety», «fucan», «fucosan» and «sulfated fucan» are equivalent for the purpose of the present description.

According to a preferred embodiment, the invention refers to any fucoidan entity exhibiting high affinity, specificity and/or selectivity for selectins and therefore for thrombus. In the context of the present invention, when a fucoidan moiety is used as a vectorizing agent, it confers its specificity/selectivity/affinity property to the molecule, and the molecule becomes "thrombus-targeted" (i.e., the molecule specifically and/or efficiently interacts with and/or binds to selectins and fibrin). The terms "binding affinity" and "affinity" are used herein interchangeably and refer to the level of attraction between molecular entities. Affinities can be expressed quantitatively as dissociation constant ($K_D$), or its inverse, the association constant ($K_A$).

According to the invention, the term «about» can be understood as more or less 10%.

According to the invention, «thrombotic diseases» and «thrombotic disorders» are diseases and/or disorders which are associated with the appearance, or persistence, of undesirable intravascular blood clot and/or thrombus.

Thrombotic disorders and diseases according to the invention may, for instance, result in the formation of venous thrombosis such as deep vein thrombosis, portal vein thrombosis, renal vein thrombosis, jugular vein thrombosis, or cerebral venous sinus thrombosis. In some cases, said thrombosis may lead to phlebitis, also referred herein as «thrombophlebitis», and sometimes to pulmonary embolisms. It may also involve atrial and ventricular thrombi related to heart arythmias.

They may also result in arterial thrombosis, which is often a consequence of the rupture of an atherosclerotic plaque, in which case it can be also referred as «atherothrombosis». An arterial thrombosis may, for instance, lead to a stroke, a myocardial infarction and/or an arterial embolus.

Thrombotic diseases are well-known in the art and can have various causes. They can be primary or acquired diseases. In particular, they can be hereditary, and/or linked to genetic predispositions. Examples of such diseases comprise, for instance, haemophilias, Von Willebrand disease, and other coagulopathies linked to hyper- and hypo-coagulability.

Fucoidan is able to target in vivo platelet and fibrin-containing thrombus with excellent sensibility and specificity (Rouzet et al., 2011, Radiolabeled fucoidan as a P-selectin targeting agent for in vivo imaging of platelet-rich thrombus and endothelial activation. J Nucl Med).

According to the invention an «aminofucoidan» is a fucoidan moiety, which is aminated by a covalent linkage between the reducing end of the said fucoidan moiety and a chemical group comprising one (mono-amine fucoidan) or more amino groups ($-NH_2$) (poly-amine fucoidan) such as primary amine groups or guanidine groups. Preferably, said chemical group only comprises, as terminal substituent(s), one or more amino groups ($-NH_2$).

Even more preferably, said chemical group only comprises, as terminal substituent(s) one or more primary amines.

According to the invention, an amino group ($-NH_2$) refers to any chemical group with a free ($-NH_2$) radical, in particular primary amine groups and guanidine groups, and more particularly primary amine groups. In a non-limitative way, a chemical group may be selected in the group consisting in lysine, arginine, ornithine, or γ-aminobutyric acid.

According to the invention, a "terminal substituent" refers to any substituent at the end of an hydrocarbon chain.

According to the invention, an «hydrocarbon chain» may in particular comprise between 1 and 44 carbon atoms, which includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44 carbon atoms, more particularly between 1 and 22 carbon atoms, and even more particularly between 1 and 10 carbon atoms.

According to a preferred embodiment, said chemical group comprises as terminal substituent(s), only terminal substituent(s) which consist(s) in a primary amine group. Thus, said aminofucoidan can be also referred herein as a "lysine-like/-mimetic primary amine ended modified fucoidan".

According to the invention, the aminofucoidan is a fucoidan which is modified on its reducing end. Because of it, the biological activity of the said fucoidan, which is dependent on the quantity and the distribution of sulfate groups along its chain, is not disturbed. However it is also possible to introduce additional primary amines directly onto the hydroxyl groups of fucoses composing said chain.

Thus, according to a particular embodiment, said fucoidan comprises primary amine containing groups covalently linked to the fucoidan chain.

According to that particular embodiment, said chain comprises on average between 1 and 10 primary amine containing groups per fucoidan chain, which includes 1, 2, 3, 4, 5, 6, 7, 8, 9 and 10 primary amine containing groups.

According to the invention, an "heteroatom" refers to an atom which is preferably selected from nitrogen (N), sulphur (S) and oxygen (O), and even more preferably selected from nitrogen and oxygen.

Thus, the present invention provides bipolar molecular platform and methods for preparing said bipolar vectors, also referred herein as aminofucoidans.

It is shown, according to the invention, that said bipolar vectors have two main characteristics:
one pole (anionic fucoidan) is able to vectorize to the thrombus,
one pole is able to interact with and protect t-PA through at least one primary amine binding function.

Thus, the invention relates to a complex between an aminofucoidan and a tissue plasminogen activator (t-PA). Said complex is a non-covalent complex.

In particular, targeting P-selectin (which is expressed at the surface of platelets) by a fucoidan moiety advantageously increases the local concentration of t-PA at or near the thrombus, which is then be responsible for an increased rate of fibrinolysis.

Advantageously, the primary amine at one pole of the aminofucoidan is part of, or alternatively mimics an aminoacid or a poly-aminoacid, in particular a lysine, a polylysine, or a lysine derivative. Such lysines, polylysines or lysine derivatives, serve as anchor residues between t-PA, plasminogen and fibrin.

Unless specified otherwise, an "amino acid", such as a "lysine" refers both to an amino acid and its derivatives.

In a non-limitative way, the amine pole may also involve a primary-amine containing moiety able to bind t-PA such as lysine, arginine, ornithine, or γ-aminobutyric acid.

Of course, the amino acid, or polyamino acid may be coupled to the fucoidan by any method known in the art, as long as the resulting aminofucoidan comprises at least one free amino group (—NH$_2$), such as a primary amine or a guanidine group, as a terminal substituent.

According to a preferred embodiment, an amino acid or a polyamino acid is coupled to a fucoidan, or to a linker L through an amide group.

Without wishing to be bound by any particular theory, the applicant believes that the non-covalent binding of t-PA to the amine-moiety of the compound is assumed to protect it from serpins and to allow it to be delivered to fibrin.

The applicant also believes that linking a fucoidan moiety to t-PA through an amino group, such as a primary amine, in particular aminoacids and aminoacid derivatives, induces a conformational change within the t-PA. This conformational change may then protect its active site from circulating inhibitors, and thus increase both the half-life and the bioavailability of a t-PA/aminofucoidan complex towards the thrombus.

According to the invention, aminoacids and/or their derivatives may have a L-configuration or a D-configuration, in particular a L-configuration.

According to the invention, an «aminoacid derivative» is a modified amino acid having a L-configuration or a D-configuration, in particular a L-configuration, and at least one free amino group, in particular a free primary amine, preferably two or more than two free primary amines.

A modified aminoacid is an aminoacid, wherein the side chain is optionally interrupted or substituted by one or more chemical group(s), identical or different.

Unless specified, an «aminoacid» according to the invention may encompass both the said «aminoacid» and its derivatives.

Advantageously, aminoacids may be covalently linked together by peptide bonds (or amide groups) in order to form polyaminoacids.

Polyaminoacid(s) is/are advantageously composed of 1, 2, 3, 4, 5 or 6 amino acids, in particular 2 or 4 amino acids.

In particular, polyaminoacids may be selected in the list consisting of: polylysines, polyarginines, polyglutamines, polycitrullines, polyornithines, and preferably polylysines.

When the fucoidan moiety is linked to t-PA through poly-lysine(s), said poly-lysine(s) is/are advantageously composed of 1, 2, 3, 4, 5 or 6 lysines, in particular 2 or 4 lysines.

Thus, dendrimers of lysines are also considered by the invention as "lysine derivatives". If not commercially available, they can be synthesized according to the protocol described in Kim & Zimmerman et al., (Y. Kim and SC Zimmerman, 1998, «Applications of dendrimers in bioorganic chemistry», Current Opinion in Chemical Biology, vol. 2, pp 733-742).

As mentioned above, vectorisation with said aminofucoidan allows for an increase of t-PA concentration at or near the thrombus, and protects said t-PA during its plasmatic delivery. Thus, said vectorization has the double advantage of increasing the local concentration of t-PA, but also of protecting t-PA from other compounds and/or inhibitors such as PAI-1.

Thus, according to one embodiment, the invention relates to a vector having t-PA binding property consisting of a fucoidan moiety which is aminated by a covalent linkage between the reducing end of the said fucoidan moiety and a chemical group comprising one or more amino groups.

According to the invention, the term «reducing end» is the end where the anomeric carbon atom (C1 for an hexose such as glucose and C2 for a pentose such as fructose) is free and has not been used to form a glycosidic bond.

According to a particular embodiment, said vector is a compound of formula (I):

FUCO-C1-[NH]$y$-[L]$z$-[NH]$x$-R1     (I), wherein
"FUCO" means a fucoidan moiety, optionally containing one or more primary amine groups covalently linked to the fucoidan chain,
x, y and z are independent integers meaning 0 or 1,
C1 is the carbon atom at position 1 of the saccharide unit located at the reducing end of the fucoidan moiety,
L is a linker, and
R1 is a chemical group comprising one or more amino groups, or consisting in one amino group,
L and R1 are independent and may be equal or different.

A «linker» L may refer to any chemical group, which includes chemical groups with and without primary amines.

According to a more particular embodiment, said vector is a compound of formula (I), wherein y and z mean 0.

Thus, according to said embodiment, the said vector is a compound of formula (I'):

FUCO-C1-[NH]x-R1      (I'), wherein

"FUCO" means a fucoidan moiety, optionally containing one or more primary amine groups covalently linked to the fucoidan chain, x is an integer meaning 0 or 1, C1 is the carbon atom at position 1 of the saccharide unit located at the reducing end of the fucoidan moiety, L is a linker, and R1 is a chemical group comprising one or more amino groups, or consisting in one amino group, L and R1 are independent and may be equal or different.

In some embodiments, the said vector is a compound of formula (I) or (I'), wherein:

R1 is a chemical group comprising or consisting in a primary-amine ended, linear or branched hydrocarbon chain; an aminoacid; a polyaminoacid; and/or a chemical group selected in the list comprising, or consisting in: lysine, polylysine, arginine, polyarginine, ornithine, polyornithine, γ-aminobutyric acid, polyamines, polyetheramines, or any other chemical group comprising a guanidine group or a primary amine, wherein:

the said chemical group is optionally interrupted by one or more non aromatic hydrocarbon ring(s) having 5 or 6 carbon atoms, and preferably not more than one non aromatic hydrocarbon ring having 5 or 6 carbon atoms, the said chemical group is optionally interrupted by one or more heteroatoms, the said chemical group is optionally containing one or more amide groups and/or one or more ester groups, in particular one or more amide groups, the said chemical group is optionally substituted by one or more amine groups, the said chemical group is optionally interrupted and/or substituted by one or more group(s), identical or different, and selected from: (a) a linear or branched hydrocarbon chain, (b) an aminoacid or a polyaminoacid (c) a polyamine or a polyetheramine, (d) a γ-aminobutyric acid (e) a guanidine group and (f) a primary amine.

According to one embodiment, L is a linker comprising or consisting in a primary-amine ended, linear or branched hydrocarbon chain; an aminoacid; a poly-aminoacid; and/or a chemical group selected in the list comprising, or consisting in: lysine, polylysine, arginine, polyarginine, glutamine, polyglutamine, citrulline, polycitrulline, ornithine, polyornithine, γ-aminobutyric acid, polyamines, polyetheramines, or any other chemical group comprising a guanidine group or a primary amine, wherein:

the said chemical group is optionally interrupted by one or more non aromatic hydrocarbon ring(s) having 5 or 6 carbon atoms, and preferably not more than one non aromatic hydrocarbon ring having 5 or 6 carbon atoms, the said chemical group is optionally interrupted by one or more heteroatoms, the said chemical group is optionally containing one or more amide groups and/or one or more ester groups, in particular one or more amide groups, the said chemical group is optionally substituted by one or more amine groups, the said chemical group is optionally interrupted and/or substituted by one or more group(s), identical or different, and selected from: (a) a linear or branched hydrocarbon chain, (b) an aminoacid or a polyaminoacid (c) a polyamine or a polyetheramine, (d) a γ-aminobutyric acid (e) a guanidine group and (f) a primary amine.

According to another particular embodiment, said vector is a compound of formula (I) or (I'), wherein:

R1 is a chemical group comprising or consisting in a primary-amine ended, linear or branched hydrocarbon chain; an aminoacid; a poly-aminoacid; and/or a chemical group selected in the list comprising, or consisting in: lysine, polylysine, arginine, polyarginine, glutamine, polyglutamine, citrulline, polycitrulline, ornithine, polyornithine, γ-aminobutyric acid, polyamines, polyetheramines, or any other chemical group comprising a guanidine group or a primary amine.

According to another particular embodiment, said vector is a compound of formula (I) or (I'), wherein R1 or L is substituted by 1 to 4 amine groups, which means 1, 2, 3 or 4 amine groups.

According to another particular embodiment, said vector is a compound of formula (I) or (I'), wherein R1 and/or L is substituted by 1 to 4 amide groups and/or 1 to 4 ester groups, which means 1, 2, 3 or 4 amine groups and/or 1, 2, 3, or 4, ester groups.

According to a more particular embodiment, the said vector is a compound of formula (I) or (I'), wherein L means a linear or branched hydrocarbon chain, in particular a linear hydrocarbon chain, of 1 to 22 carbon atoms, in particular 1 to 10 carbon atoms, and more particularly 1 to 5 carbon atoms, wherein:

the said hydrocarbon chain is optionally interrupted by one or more heteroatoms, the said hydrocarbon chain is optionally containing one or more amide groups, the said hydrocarbon chain is optionally substituted by one or more amine groups.

According to a particular embodiment, L is selected in a group consisting in $(CH_2)_2$, $(CH_2)_3$ and $(CH_2)_2$—NH—$(CH_2)_2$, and preferably $(CH_2)_3$ and $(CH_2)_2$—NH—$(CH_2)_2$ Advantageously, when R1 is a chemical group chosen in a list of aminoacids or polyaminoacids, the said aminoacid or polyaminoacid may be linked to the fucoidan through either (a) the C-terminal end (—COOH), or (b) the N-terminal end (—NH2) of the said aminoacid.

Preferably, the aminoacid or polyaminoacid is linked to the fucoidan through the C-terminal end (—COOH) of the said aminoacid.

According to the invention, the "N-terminal end" or "C-terminal end" of an aminoacid or a polyaminoacid must be understood as respectively the primary amine (—NH2) and the carboxylic group (—COOH) born by the a carbon of this aminoacid.

Of course, when the aminoacid or polyaminoacid is linked through its N-terminal end (—NH2), one has to choose an amino acid, or a derivative, which bears at least one additional free primary amine or free guanidine group as a terminal substituent, in order to obtain an aminofucoidan bearing at least one free amino group suitable for vectorizing t-PA to the thrombus.

According to another particular embodiment, said vector is a compound of formula (I) or (I'), wherein —[NH]x-R1 is selected from the group consisting of:

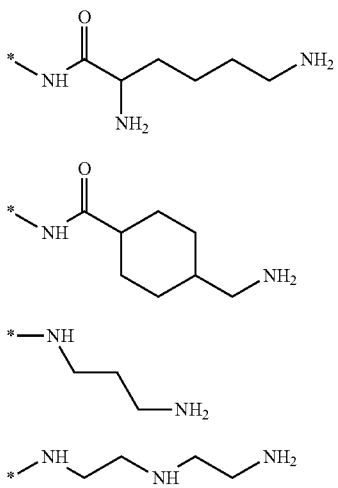

According to a preferred embodiment, said vector is selected from the group consisting of:

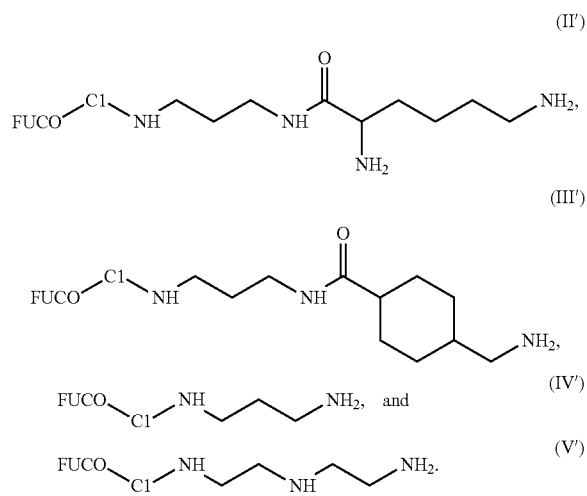

wherein
"FUCO" means a fucoidan moiety, optionally containing one or more primary amine groups covalently linked to the fucoidan chain,
C1 is the carbon atom at position 1 of the saccharide unit located at the reducing end of the fucoidan moiety.

According to a particular embodiment, said vector is a compound of formula (I) or (I') which comprises a poly-lysine or a lysine derivative, in particular a poly-lysine.

According to this particular embodiment, —[NH]x-R1 may be of formula (VI):

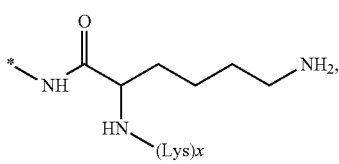

wherein:
«Lys» is a lysine or a lysine derivative, and preferably a lysine,
x is at least equal or superior to 1, preferably equal to 2, 3, 4, 5 or 6 and most preferably equal to 2 or 4.

Thus, according to a preferred embodiment, said vector is a compound of formula (VI'):

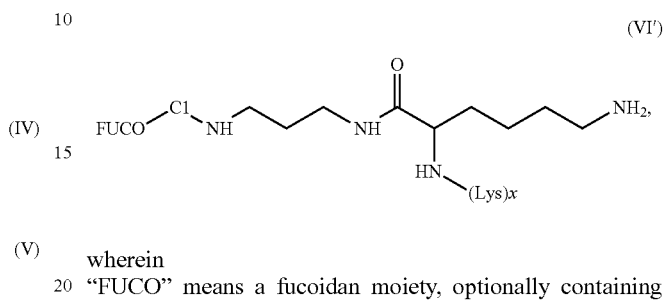

wherein
"FUCO" means a fucoidan moiety, optionally containing one or more primary amine groups covalently linked to the fucoidan chain,
C1 is the carbon atom at position 1 of the saccharide unit located at the reducing end of the fucoidan moiety.
«Lys» is a lysine or a lysine derivative, and preferably a lysine,
x is at least equal or superior to 1, preferably equal to 2, 3, 4, 5 or 6 and most preferably equal to 2 or 4.

According to a preferred embodiment, aminoacids such as lysines are covalently linked through amide groups, to form polylysines or dendrimers. Said polylysines or dendrimers can be obtained by any method known in the art.

According to another particular embodiment, —[NH]x-R1 and/or a lysine derivative can be of formula (VII):

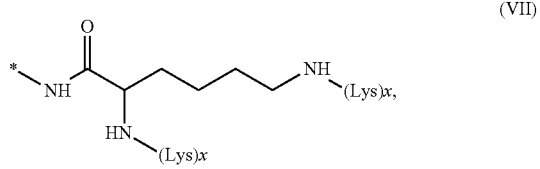

wherein
«Lys» is a lysine or a lysine derivative, and preferably a lysine,
x is at least equal or superior to 1, preferably equal to 2, 3, 4, 5 or 6 and most preferably equal to 2 or 4.

Thus, said formula (VII) can be part of a dendrimer of lysines.

Apart from lysines and polylysines, other aminoacids and polyaminoacids may be coupled to the fucoidan. In particular, the invention also relates to vectors of general formula (I) or (I'), wherein R1 is derived from an arginine, a polyarginine and/or any other guanidine-containing chemical group.

Polyamines and Polyetheramines

According to another embodiment, the said vector is a compound of formula (I) or (I'), wherein R1 is derived from a polyamine or a polyetheramine. Polyetheramines may be either a monoamine polyetheramine, or a polyamine polyetheramine, such as a diamine or a triamine polyetheramine, and preferably a polyamine polyetheramine.

Advantageously, the polyamine and/or polyetheramine may be coupled to the fucoidan or a linker L through any one of its free primary amines.

According to a particular embodiment, the said vector is a compound of formula (I) or (I'), wherein R1 is selected from the group consisting of polyetheramines.

Such polyetheramines are well known in the art and may be sold under the name of JEFFAMINE® polyetheramines.

Polyetheramines contain primary amine groups attached to the end of a polyether backbone. The polyether backbone is based on either propylene oxide (PO) units, ethylene oxide (EO) units, or mixed PO/EO units.

The polyether backbone of such polyetheramines may thus vary depending on a given PO/EO unit ratio. Polyetheramines may comprise primary amine groups at one end (also referred herein as monoamines), at two ends (diamines) or at three ends (triamines).

A general formula (VIII) of monoamine polyetheramines suitable for the invention is given herebelow:

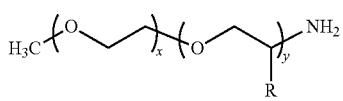

(VIII)

wherein R is H for (EO), or $CH_3$ for (PO), and preferably $CH_3$,
wherein x and y may be equal or different.

Such monoamines may be prepared by reaction of a mono-alcohol initiator with EO and/or PO, followed by conversion of the resulting terminal hydroxyl groups to amines.

According to said embodiment, when R is equal to $CH_3$, the y/x ratio may in particular range from 0.1 to 10, in particular from 0.15 to 9.

Advantageously, a monoamine polyetheramine of formula (VIII) may have an average molecular weight ranging from 500 to 5000 g/mol$^{-1}$, in particular ranging from 600 to 2000 g/mol$^{-1}$.

Monoamine polyetheramines which correspond to the above-mentioned general formula are sold as JEFFAMINE® monoamines (M series), for instance M-600, M-1000, M-2005 and M-2070.

A first general formula (IX) of diamine polyetheramines suitable for the invention is given herebelow:

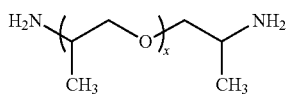

(IX)

wherein x is an integer which may range from 1 to 100, in particular from 2 to 70.

Advantageously, a diamine polyetheramine of formula (IX) may have an average molecular weight ranging from 100 to 5000 g/mol$^{-1}$, in particular ranging from 200 to 4000 g/mol$^{-1}$.

A second general formula (X) of diamine polyetheramines suitable for the invention is given herebelow:

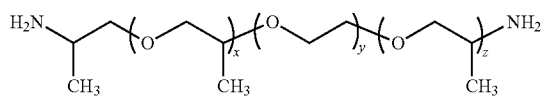

(X)

wherein x, y and z may be equal or different,
wherein y may range from 1 to 50, in particular from 2 to 40,
wherein x and z may range from 0 to 10, in particular from 0 to 6,
wherein the sum of x and z may optionally range from 1 to 6.

Advantageously, a diamine polyetheramine of formula (X) may have an average molecular weight ranging from 100 to 5000 g/mol$^{-1}$, in particular ranging from 200 to 2000 g/mol$^{-1}$.

A third general formula (XI) of diamine polyetheramines suitable for the invention is given herebelow:

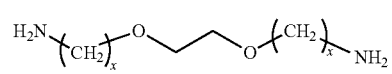

(XI)

wherein x may range from 1 to 5, in particular from 1 to 3, and preferably 2 or 3.

Advantageously, a diamine polyetheramine of formula (XI) may have an average molecular weight ranging from 100 to 500 g/mol$^{-1}$, in particular ranging from 100 to 200 g/mol$^{-1}$.

Diamine polyetheramines may be commercialized as JEFFAMINE® diamines (D, ED, EDR series), for instance D-230, D400, D-2000, D-4000, HK-511, ED-60D, E 90D, ED-20D3, EDR-148, EDR-176.

A general formula (XII) of triamine polyetheramines suitable for the invention is given herebelow:

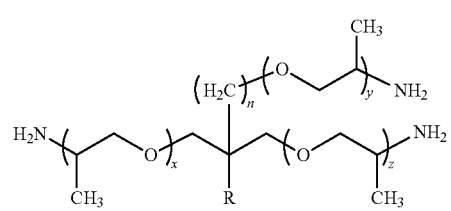

(XII)

wherein n may be equal to 0 or 1,
wherein R may represent H or $C_2H_5$,
wherein x, y and z may be equal or different and may range from 0 to 100, in particular from 0 to 85,
wherein the sum of x, y and z ranges from 5 to 100, in particular from 5 to 85.

Triamine polyetheramines may be commercialized as JEFFAMINE® triamines (T series), for instance T-403, T-3000, T5000.

Preferably, polyetheramines may be chosen in the group consisting in polyamine polyetheramines, and more preferably diamine or triamine polyetheramines, such as polyetheramines of formulas where x, y and z are ranging from 2 to 10.

Alternatively, the said vector is a compound of formula (I) or (I'), wherein R1 is derived from a polyamine such as spermin or spermidin, diaminopropane or diethylenetriamine.

Spermin is a polyamine of formula (XIII)

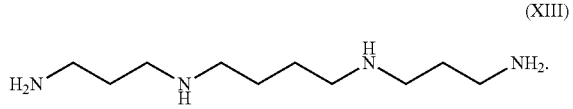 [SMILES: NCCCNCCCCNCCCN]
(XIII)

Spermidin is a polyamine of formula (XIV):

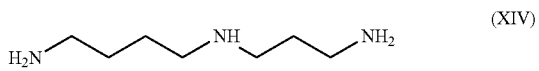
(XIV)

A polyamine or a polyetheramine is linked to the fucoidan or a linker L using any method known in the art or described hereafter, or as shown in the examples.

For instance, a polyamine or a polyetheramine may be linked to a fucoidan via reductive amination by end-to-end coupling reaction between the aldehyde function of the reducing sugar of the fucoidan and the amine function of a polyetheramine, such as in Belbekhouche et al. (Belbekouche S. et al., 2013, Carbohydrate Polymers, http://dx.doi.org/10.1016/j.carbpol.2013.02.032).

Advantageously, compounds of the invention can be further obtained according to methods defined herebelow, or as illustrated in example 1, 2, 3 and 4.

Vectorized t-PA

Thus, the invention also relates to a method for preparing a vectorized t-PA comprising the steps of:
a) providing a vector of the invention,
b) providing t-PA, and
c) bringing into contact the vector provided at step a) with the t-PA provided at step b), so as to obtain complexes between the said vector and t-PA.

According to one embodiment, the invention further relates to a vectorized t-PA comprising complexes of a vector according to the invention, with t-PA.

According to one embodiment, a composition comprising a vector or a vectorized-tPA of the invention is considered in a substantially pure form.

A substantially pure composition as defined above, and comprising a vector or a vectorized t-PA according to the invention may contain, as the major form, a vector or a vectorized-t-PA of which the fucoidan is aminated at its reducing end, compared to either the total amount of fucoidan in the said composition, or to the total amount of aminated fucoidan in the said composition.

According to said embodiment, a substantially pure composition may contain at least 50% in molar ratio of a vector that is aminated at its reducing end, wherein said molar ratio is based on the total amount of fucoidan in the said composition.

Alternatively, a substantially pure composition may contain at least 50% in molar ratio of a vector that is aminated at its reducing end, wherein said molar ratio is based on the total amount of aminated fucoidan in the said composition.

Thus a substantially pure composition as defined above may contain at least 50% in molar ratio, and preferably more, of a vector that is aminated at its reducing end, which includes 50%, 51%, 52%, 53%, 54%, 55%, 56%, 57%, 58%, 59%, 60%, 61%, 62%, 63% 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or even 100% in molar ratio.

As mentioned before, the presence of amines functions at one pole of the bipolar vector allows it to interact with and protect t-PA and plasminogen.

Advantageously, it is possible to vary the average amount of vector which can interact with t-PA as a complex, or in the context of a pharmaceutical composition.

According to a particular embodiment, the vectorized t-PA may have a molar ratio of vector to t-PA ranging from 40:1 to 1:1; preferably from 20:1 to 3:1, and most preferably from 15:1 to 5:1.

According to a preferred embodiment, the molar ratio of vector to t-PA is of about 10:1 when the vector is a mono-amine fucoidan, and about 5:1 when the vector is a poly-amine fucoidan.

Thus, a vectorized t-PA according to the invention can be intended for use as a medicament. In particular, said vectorized t-PA can be intended for use as an active ingredient for preventing or treating a thrombus in a subject.

From the above, the man skilled in the Art understands that a vector or a vectorized t-PA of the invention, or alternatively a pharmaceutical composition comprising a vector or a vectorized t-PA of the invention, should be suitable for an administration to a subject in need thereof.

In particular, such a pharmaceutical composition should be suitable and/or compatible with a parenteral administration to a subject in need thereof.

Preferably a pharmaceutical composition of the invention should be sterile, and/or devoid of microorganisms.

Fucoidan Moieties

Fucoidans (also called fucos, fucosans or sulfated fucans) are sulfated polysaccharides with a wide spectrum of biological activities, including anticoagulant, antithrombotic, antivirus, antitumor, immunomodulatory, anti-inflammatory, and antioxidant activities. Fucoidans are found mainly in various species of brown seaweed (B. Li et al, Molecules, 2008, 13: 1671-1695; M. Kusaykin et al, Biotechnol. J., 2008, 3: 904-915).

According to a particular embodiment, a fucoidan or a fucoidan moiety suitable for the invention is obtained from seaweed, and in particular brown seaweed.

Variant forms of fucoidans have also been found in marine animal species, including the sea cucumber. Thus, compared to other sulfated polysaccharides, fucoidans are widely available from various kinds of cheap sources, and easily obtained using methods of extraction known in the art (C. Colliec et al, Phytochemistry, 1994, 35(3):697-700).

These methods of extraction generally yield fucoidans with molecular weights in the 70-800 kDa range. Processes have also been developed to depolymerize high molecular weight fucoidans in low molecular weight fucoidans, e.g., lower than about 20 kDa (EP 0403 377B, U.S. Pat. No. 5,321,133), or lower than about 10 kDa (EP 0 846 129 B; U.S. Pat. No. 6,028,191; A. Nardella et al, Carbohydr. Res., 1996, 289: 201-208).

According to a particular embodiment, a fucoidan or a fucoidan moiety suitable for the invention is obtained according to the method of extraction and depolymerization described in example 1.

According to another embodiment, fucoidans can be obtained commercially from the following companies: Fucoidan from Sigma-Aldrich company (USA): Crude fucoidan (from *Fucus vesiculosus*) ref F5631, CAS Number 9072-19-9. MM=20,000-200,000 g/mol; Fucoidan from Algues-et-Mer company (France): Asphyscient® (from *Ascophyllum nodosum*), on request, MM=5,000-10,000 g/mol; Fucoidan from Kraeber GmbH (Germany): on request, LMWF, 8,500 g/mol, HMWF, 600,000 g/mol, from different brown algae.

Fucoidans are generally made of a linear backbone built up of α-1,3-L Fuc or alternating α-1,3-L Fuc, α-1,4-L Fuc, or α-1,2-L Fuc which can be present in the backbone branching. Sulfate groups occupy the C-2 and/or C-3 or C-4 of fucose.

According to a particular embodiment, fucoidans are α-1,2- or α-1,3-linked L-fucose polymers that are mainly sulfated on position 4 and position 2 or 3 following the glycosidic linkage. However, besides fucose and sulfate residues, fucoidans also contain other monosaccharides (e.g., mannose, galactose, glucose, xylose, etc) and uronic acid groups. It is known in the art that the structure of fucoidans from different brown algae varies from species to species.

When fucoidans contain uronic acid (UA) and other hexoses, the structure of said fucoidans may be built around a polysulfated poly-L fucose linear backbone bearing substituents selected in a group consisting of: uronic acid, an hexose (1 unit), a sulfate group, and an acetyl group. As an example, the schematic widely admitted structure of fucoidan extracted from the brown seaweed *Ascophyllum nodosum* is given in Berteau & Mulloy or Pomin & Mourao (O. Berteau and B. Mulloy, 2003, Glycobiology, 13(6) 29-40, DOI: 10.1093/glycob/cwg058; V. Pomin and PAS Mourao, 2008, Glycobiology 18(12) 1016-1027, review, DOI: 10.1093/glycob/cwn085).

According to a preferred embodiment, a fucoidan can be composed of a repeating unit of formula (IX):

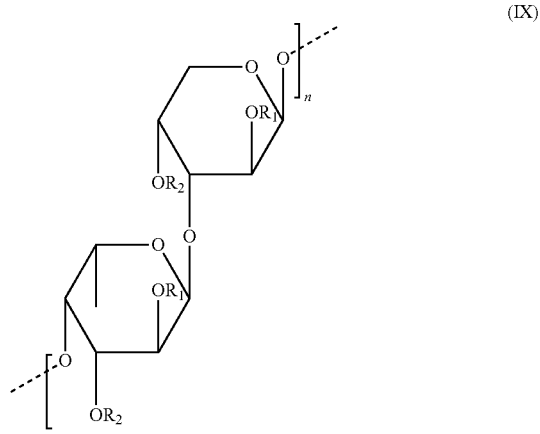

(IX)

wherein
$R_1$ and $R_2$ mean, one independently from the other: H, a sulfate group, an acetyl group, an hexose and/or uronic acid,
n is equal or superior to 1.

Furthermore, the structure of fucoidans can also be chemically modified. For example, methods have been developed to increase the percentage of sulfate groups of fucoidans in order to obtain oversulfated fucoidans or oversulfated fucoidan fragments (T. Nishino et al, Carbohydr. Res., 1992, 229: 355-362; S. Soeda et al, Thromb. Res., 1993, 72: 247-256).

According to a particular embodiment, the fucoidan or fucoidan moiety is polysulfated.

According to a more particular embodiment, said polysulfated fucoidan has a sulfate-to-sugar ratio superior to 1, in particular superior to 1.2, preferably superior or equal to 1.9.

According to a particular embodiment, the fucoidan or fucoidan moiety comprises primary amines covalently linked to the fucoidan chain, but not to the reducing end of the said fucoidan.

Alternatively, when the fucoidan is an aminofucoidan, the said aminofucoidan further comprises primary amines covalently linked to the fucoidan chain.

According to said embodiments, the said fucoidan or aminofucoidan may comprise on average between 1 and 10 primary amines per fucoidan chain.

According to a more particular embodiment, the said fucoidan or aminofucoidan is aminated on a free hydroxyl group of the fucoidan chain, for instance of a fucose, by a primary amine.

Said amination, which is distinct from an amination at the reducing end of the said fucoidan can be, for instance, achieved using the protocol defined in example 1.

Fucoidan moieties suitable for use in the present invention are fucoidan moieties that have some degree of attraction for selectins, in particular P-selectin, and that can play a targeting role when they are part of a vectorizing agent. Preferably, fucoidan moieties are stable, non-toxic entities that retain their affinity/specificity/selectivity properties under in vitro and in vivo conditions. In preferred embodiments, fucoidan moieties exhibit high affinity and specificity for selectins, i.e., they specifically and efficiently interact with, bind to, or associate with selectins. Suitable fucoidan moieties include fucoidans that exhibit affinity and specificity for only one of the selectins (i.e., for L-selectin, E-selectin or P-selectin) as well as fucoidans that exhibit affinity and specificity for more than one selectin, including those moieties which can efficiently interact with, bind to or associate with all three selectins. Preferably, the interaction between a selectin and a fucoidan moiety as part of a vectorizing agent is strong enough for at least the time necessary to vectorize t-PA to a thrombus. In certain embodiments, a suitable fucoidan moiety interacts with a selectin with a dissociation constant ($K_D$) between about 0.1 nM and about 500 nM, preferably between about 0.5 nM and about 10 nM, more preferably between about 1 nM and about 5 nM.

Fucoidans can be of high molecular weight or low molecular weight.

A «molecular weight», according to the invention, relates to the «weight average molecular weight», or Mw.

A «low molecular weight fucoidan», according to the invention, relates to any fucoidan with an average molecular weight equal or lower than 20000 Da, in particular within a range between 2000 and 20000 Da.

A «high molecular weight fucoidan», according to the invention, relates to any fucoidan with an average molecular weight superior to 20000 Da, in particular within a range between 20000 and 600000 Da.

In certain embodiments, the fucoidan moiety has an average molecular weight of about 2000 to about 8000 Da. In other embodiments, the fucoidan moiety has an average molecular weight of about 20000 to about 70000 Da. In yet other embodiments, the fucoidan moiety has an average molecular weight of about 100000 to about 500000 Da.

According to one embodiment, the fucoidan moiety has an average molecular weight which is lower than 100000 Da, and preferably lower than 20000 Da, for instance between 2000 and 20000 Da.

According to another embodiment the fucoidan moiety has an average molecular weight ranging from 2000 Da to 15000 Da According to a particular embodiment, fucodains are chosen among low molecular weight fucoidans, such as the ones described in WO2010116209.

Methods for Obtaining Amino-Fucoidans

Herebelow are taught methods for obtaining aminofucoidans according to the invention. The man skilled in the art may easily adapt said methods at his convenience for obtaining particular aminofucoidans.

In a non-limiting way, a strategy for synthesizing amine derivatives of fucoidans, also referred herein as «aminofucoidans», can be a two-step process:

1. Reductive Amination of Fucoidan at the Reducing End.
a. Schiff base (imine) formation between an aldehyde of the polysaccharide and a primary amine of a spacer, namely a «bridging compound» such as diaminopropane (DAP). This reaction is reversible in an aqueous medium.
b. Reduction of imine into an amine to block the reversibility of said reaction.

2. Coupling of Amino-Acid Residues or Derivatives by Reacting the Carboxylic Function (—COOH) at their C-Terminal Extremity and the Primary Amine of the Diaminopropane which has been Fixed on the Fucoidan Moiety in Step 1.

That second step is achieved, for instance, by using activating coupling reagents such as NHS and EDC. Said NHS and EDC reagents are commercially available and sold by companies such as Sigma Aldrich (Ref. 130672 or Ref. 03449).

This two-step protocol has the advantage of being specific to the reaction between the aldehyde group from the reducing end of the polysaccharidic chain and the primary amine of the spacer. It has the advantages of (i) being simple and robust and (ii) to limit the structural modification of the polysaccharidic moiety to its end, to avoid the risk of impairing the biological activity when chemical modifications are performed within the chain (O. Roger et al., 2002, «Polysaccharide labelling: impact on structural and biological properties», *Carbohyd. Pol.*, 50(3)273-278). The second step is a classical coupling reaction between a primary amine function and a carboxylic function in an aqueous medium, and is thus easy to follow (G. T. Hermanson, «Bioconjugate Techniques» Academic Press, 2008).

Furthermore, robustness of said protocol advantageously allows to replace diaminopropane (DAP) by other «spacers», or linkers L, in order to obtain any aminofucoidan comprising at least one free amino group at its end, in particular a primary amine.

A «spacer», according to the invention, comprises, and preferably consists in any compound having at least two free amino groups, such as free primary amines.

Advantageously, said diaminopropane (DAP) can be substituted by any compound comprising two free primary amines.

Thus, the invention further contemplates aminofucoidans of which the spacer is not diaminopropane (DAP), and/or of which the reducing end is not functionalized by a diaminopropane.

Thus the invention also relates to a vector having t-PA binding property consisting of a fucoidan moiety which is aminated by a covalent linkage between the reducing end of the said fucoidan moiety and a chemical group comprising one or more amino groups, wherein said chemical group is not obtained directed from the covalent linkage between the reducing end of the said fucoidan moiety and diaminopropane.

According to a particular embodiment, diaminopropane (DAP) of formula ($NH_2$—$(CH_2)_3$—$NH_2$) can be substituted in a first step by other compounds containing free primary amines such as, for instance polyamines and in particular diethylenetriamine, (DETA) of formula ($NH_2$—$(CH_2)_2$—NH—$(CH_2)_2$—$NH_2$).

It is understood that the invention also contemplates aminofucoidans of which the spacer is not diethylenetriamine (DETA), and/or of which the reducing end is not functionalized by a diethylenetriamine.

Thus the invention also relates to a vector having t-PA binding property consisting of a fucoidan moiety which is aminated by a covalent linkage between the reducing end of the said fucoidan moiety and a chemical group comprising one or more amino groups, wherein said chemical group is not obtained directed from the covalent linkage between the reducing end of the said fucoidan moiety and diethylenetriamine.

According to a particular embodiment, amino-acid residues or derivatives which can be coupled in the second step of reaction may be selected in a group comprising, and preferably consisting in aminocaproic acid, tranexamic acid, a lysine or a poly/oligolysine, or a lysine derivative.

Other strategies, which could be defined as "alternative strategies", are also reported. Although they can substitute the two-step method as defined above, they are also hindered by a few limitations.

Three of those "alternative strategies" are developed herebelow.

A. Formation of a Lactone

In one particular embodiment, an aminofucoidan can be obtained through the formation of a lactone, such as in Hernandez et al. (Hernandez et al., 2007, "Synthesis, reactivity, and pH-responsive assembly of new double hydrophilic block copolymers of carboxymethyldextran and poly (ethylene glycol)", Polymer 48, pp 921-930).

According to this particular embodiment, the method comprises the steps of:

1. Formation of a lactone at the reducing end of the fucoidan by oxidation of the reducing sugar with a mixture of di-iodure and potash.

2. Reaction of a molecule bearing a primary amine, such as an amino-acid residue or a derivative, through said amine with the lactone in order to form an amide bond.

According to said embodiment, the oxidized sugar must be free of any substituent, so that oxidation remains efficient, which is not necessarily true for all sulfated fucoidans. The amine derivative which reacts with the lactone must also be in large excess. Furthermore the reaction may last for a few days at 60° C., which could alter the structure of the fucodain itself, contrarily to the dextran taught in Hernandez et al.

B. Formation of a Semicarbazone or a Thiosemicarbazone

In another particular embodiment an aminofucoidan can be obtained through the formation of a semicarbazone or a thiosemicarbazone, such as in Zhang et al. (Zhang et al., 2011, "One-pot fluorescent labeling of saccharides with fluorescein-5-thiosemicarbazide for imaging polysaccharides transported in living cells", Carbohyd. Res., 346 pp 2156-2164). Said semicarbazone can be obtained, for instance, by condensation of a semicarbazide with an aldehyde or a cetone.

When the semicarbazone is obtained through the condensation of an aldehyde (the reducing end of a polysaccharide for instance), the reaction is the following:

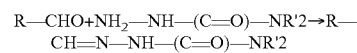

wherein R is a polysaccharide, such as a fucoidan, and wherein R' is a carbon structure, such as a fluorophore.

The semicarbazone is stabilized by reduction of the double bond C═N.

According to said embodiment, the semicarbazide may be synthesized in such a way that the R' radical contains a free amine function (—$NH_2$), in particular an amine function (—$NH_2$) which can be further coupled via EDC/NHS, with the carboxylic function of the other compounds, such as amino-acids and/or amino-acids derivatives.

C. Formation of an Oxime

In another particular embodiment an aminofucoidan can be obtained through the formation of an oxime, such as in Novoa-Carballal & Müller (Novoa-Carballal and Müller, 2012, "Synthesis of polysaccharide-b-PEG block copolymers by oxime click", Chem Comm, 48 pp 3781-3783).

Said particular embodiment relies on the so-called "click chemistry", which allows to condensate in one single step the reducing end (aldehyde) of a polysaccharide such as a fucoidan, with a R—O—$NH_2$ derivative.

According to said embodiment, the R—O—$NH_2$ derivative must be prepared from a R—OH precursor according to complex organic synthesis (Mitsonobu reaction). The oxime is efficiently formed at pH 3 and at 45° C. In those conditions, the fucoidan which is sensible to pHs inferior to 5, would have a tendency to degrade rapidly.

Thus, all the compounds which are amino-acids, such as lysines, polylysines and lysine derivatives which possess a carboxylic acid function, and which are further soluble in water can be considered for this strategy.

Also, the synthesis of aminofucoidans comprising dendrimers of lysine can be considered. According to that particular embodiment, said dendrimers should be synthesized separately and prior to the coupling step to the fucoidan.

Preferably, when poly-aminoacids such as oligolysines and/or dendrimers are considered, one should take care to prevent the formation of interpolyelectrolytes, which may result in the folding of the cationic peptidic chain onto the anionic polysaccharide (in that case the aminofucoidan), and which may reduce the water solubility of the said aminofucoidan.

Thus, the present invention also relates to aminofucoidans which can be obtained according to said methods, in particular compounds of formula (I), (I'), (II'), (III'), (IV'), (V') and (VI').

Fucoidans and aminofucoidans, according to the invention can be further characterized by their physico-chemical properties, in particular their degree of amination, their degree or mass percentage of fucose, their degree or mass percentage of uronic or glucuronic acid, their degree or mass percentage of sulfatation and their molecular weight.

Said properties must be understood as average values. Mass percentages can be expressed in %, as well as in g/100 g. Thus, the man skilled in the art will also consider preparations of fucoidans and aminofucoidans as heterogenous mixtures or preparations, which do not necessarily comprise one single type of fucoidan, or aminofucoidan, but a set of compounds related to each others according to average physico-chemical properties.

According to a particular embodiment, said aminofucoidans have a degree of amination ranging from about 0.1 $NH_2$/mol to about 3 $NH_2$/mol, in particular ranging from about 1 $NH_2$/mol to about 3 $NH_2$/mol, and preferably ranging from about 1 to about 2 $NH_2$/mol.

According to a particular embodiment, said fucoidans have a mass percentage of fucose ranging from about 30% to about 60%, in particular ranging from about 30% to about 50%.

According to a particular embodiment, said fucoidans have a mass percentage of glucuronic acid ranging from about 5% to about 40%, in particular ranging from about 10% to about 30%.

According to a particular embodiment, said fucoidans have a mass percentage of sulfate ranging from 10% to about 45%, in particular ranging from about 15% to about 40%.

According to a particular embodiment, said fucoidans have an average molecular weight which is lower than 100 000 Da, and preferably lower than 20 000 Da. According to a preferred embodiment, said fucoidans have an average molecular weight ranging from 2000 Da to 15 000 Da.

Pharmaceutical Compositions

As already mentioned above, the invention relates to a method for preparing a vectorized t-PA comprising the steps of:

a) providing a vector of the invention,
b) providing t-PA, and
c) bringing into contact the vector provided at step a) with the t-PA provided at step b), so as to obtain complexes between the said vector and t-PA.

Thus, the invention also relates to a pharmaceutical composition comprising complexes of a vector according to the invention with t-PA.

Advantageously, a pharmaceutical composition comprising said complexes can be obtained according to said method.

According to a particular embodiment, the invention also relates to a pharmaceutical composition comprising a molar ratio of vector to t-PA ranging from 40:1 to 1:1; preferably from 20:1 to 3:1, and most preferably from 15:1 to 5:1.

According to a preferred embodiment, the molar ratio of vector to t-PA in said pharmaceutical composition is of about 10:1 when the vector is a mono-amine fucoidan, and about 5:1 when the vector is a poly-amine fucoidan. Alternatively, the invention relates to a kit comprising:

a first container comprising a vector of the invention, and
a second container comprising t-PA.

A «container» suitable for the invention may be any pharmaceutical container known in the art, preferably a sterile container, which is either directly suitable for injection, or which may be suitable for preparing an injectable sample, alone or when mixed with a second container according to the invention. Examples of said containers may be selected in a group comprising pills, tablets, capsules, bottles, syringes, needles, catheters, infusion pumps, ampullas, and more generally any small sealed vial which may be used to contain and preserve a sample. Said containers may be made of glass or plastic, such as polypropylene.

Advantageously, said containers are subsequently mixed in order to achieve a specific pharmaceutical composition according to the invention.

According to this particular embodiment, the amount of vector and t-PA in each container can be easily adjusted by the man skilled in the art, in order to reach a specific ratio of vector to t-PA.

Often, pharmaceutical compositions will be administered by injection. For administration by injection, pharmaceutical compositions of thrombolytic agents may be formulated as sterile aqueous or non-aqueous solutions or alternatively as sterile powders for the extemporaneous preparation of sterile injectable solutions. Such pharmaceutical compositions should be stable under the conditions of manufacture and storage, and must be preserved against the contaminating action of microorganisms such as bacteria and fungi.

The invention further relates to a container comprising a vector of the invention, and t-PA. Advantageously, when said vector and said t-PA are formulated in an anhydrous form, such as sterile powders, the pharmaceutical composition can then be reconstituted in one single container with a suitable composition and without any additional mixing step.

Pharmaceutically acceptable carriers for administration by injection are solvents or dispersion media such as aqueous solutions (e.g., Hank's solution, alcoholic/aqueous solutions, or saline solutions), and non-aqueous carriers (e.g., propylene glycol, polyethylene glycol, vegetable oil and injectable organic esters such as ethyl oleate). Injectable pharmaceutical compositions may also contain parenteral vehicles (such as sodium chloride and Ringer's dextrose), and/or intravenous vehicles (such as fluid and nutrient replenishers); as well as other conventional, pharmaceutically acceptable, non-toxic excipients and additives including salts, buffers, and preservatives such as antibacterial and antifungal agents (e.g., parabens, chlorobutanol, phenol, sorbic acid, thimerosal, and the like). Prolonged absorption of the injectable compositions can be brought about by adding agents that can delay absorption (e.g., aluminum monostearate and gelatin). The pH and concentration of the compositions can readily be determined by those skilled in the art.

According to a preferred embodiment, the pH of a composition comprising an aminofucoidan should be comprised between 5 and 8.

Sterile injectable solutions are prepared by incorporating the active compound(s) and other ingredients in the required amount of an appropriate solvent, and then by sterilizing the resulting mixture, for example, by filtration or irradiation. The methods of manufacture of sterile powders for the preparation of sterile injectable solutions are well known in the art and include vacuum drying and freeze-drying techniques.

In general, the dosage of a vectorized t-PA (or pharmaceutical composition thereof) will vary depending on considerations such as age, sex and weight of the patient, as well as the particular pathological condition suspected to affect the patient, the extent of the disease, or the area(s) of the body to be examined. Factors such as contra-indications, therapies, and other variables are also to be taken into account to adjust the dosage of the agent to be administered. This, however, can be readily achieved by a trained physician. In general, a suitable daily dose of a vectorized t-PA (or pharmaceutical composition thereof) corresponds to the lowest amount of t-PA (or pharmaceutical composition) that is sufficient to allow prevention or treatment of thrombus in a subject.

The daily dose for administration of t-PA, such as vectorized and non-vectorized t-PA, can be expressed in molarity or as a mass. When a daily dose is expressed as a mass of administered t-PA, it must be understood in terms of "equivalent dose of t-PA".

According to the invention an "equivalent dose of t-PA" means the mass of vectorized t-PA which would be administered relatively to a non-vectorized t-PA if the two molecules had the same molecular weight. For instance, such conversion can be easily calculated by the man skilled in the art when considering the average molecular weight of a t-PA of reference (i.e. non vectorized t-PA) and the average molecular weight of a vectorized t-PA according to the invention.

To minimize this dose, it is preferred that administration be intravenous. Intravascular administration can be proximal (i.e. intraclot injection) or distal to the target site (intravenous). Advantageously, the vectorized t-PA (or pharmaceutical composition thereof) is suitable for distal administration.

A daily dose may depend upon many factors, such as the weight and the age of the patient, localization of the targeted blood clot and the administration frequency or mode, i.e. proximal or distal. For example, intraclot injection of recombinant t-PA has been proposed for the treatment of Acute Deep Venous Thrombosis, as taught in Chang et al. (Chang et al., 2011, Low Dose Once Daily, Intraclot Injections of Alteplase for Treatment of Acute Deep Venous Thrombosis, J. Vasc. Interv. Radiol., 22(8):1107-1116). According to said protocol, an intraclot injection can be efficient with an average total dose of 7.1 mg of t-PA per patient, with an average of 2.1 treatments or days of therapy.

For acute myocardial infarction (MI), vectorized t-PA can be administered for instance as an accelerated infusion (for 1½ hours), or as a 3-hour infusion.

In other embodiments, such as for treating acute ischemic stroke, the total dose may reach for instance 90 mg Thus the daily dose will depend mostly on the weight of the patient and the length of injection. For comparison, non-vectorized t-PA can be administered peripherally to a patient below 67 kg and for treating acute MI for 1 to 1 h 30 in bolus over 1-2 minutes (15 mg), and then administered (0.75 mg/kg) for 30 minutes at a dose up to 50 mg; in a last step, 0.5 mg/kg of t-PA is injected over the next 60 minutes, and preferably at a dose which does not exceed 35 mg. Accordingly, the final dose of t-PA which can be injected may reach for instance 100 mg. Advantageously, the vectorization of t-PA with aminofucoidans is susceptible to overcome the problems related to high-dose administration by lowering the minimal daily dose and thus, in particular embodiments, may allow at least a 1-log decrease, in particular embodiments at least a 2-log decrease, in terms of required daily dose.

In particular embodiments, vectorized t-PA may thus be administered as an intraclot injection for treating or preventing Acute Deep Vein Thrombosis, at a minimal daily dose equal or inferior to 7 mg, in particular equal of inferior to 5 mg, in particular equal or inferior to 2 mg, in particular equal or inferior to 1 mg for efficient clot thrombolysis.

In other embodiments, vectorized t-PA can be administered at a normal or increased daily dose without experiencing secondary symptoms which are usually associated with t-PA injection. Alternatively, said symptoms may be reduced or prevented, in comparison with a non-vectorized t-PA, when the daily dose is kept as a constant.

In particular embodiments, vectorized t-PA may thus be administered at a higher daily dose. Advantageously, said daily dose may be equal or superior to 100 mg, equal or superior to 150 mg. In particular embodiments, the daily dose may even be equal or superior to 200 mg or 300 mg.

The man skilled in the art is able to modulate said daily doses according to the needs of the patient, and depending on the condition to be treated.

EXAMPLES

The starting fucoidans which are used in the following examples were obtained from commercial sources described herebelow:

1) Fucoidan from Sigma-Aldrich company (USA): Crude fucoidan (from *Fucus vesiculosus*) ref F5631, CAS Number 9072-19-9. MM=20,000-200,000 g/mol.

2) Fucoidan from Algues-et-Mer company (France): Asphyscient® (from *Ascophyllum nodosum*), on request, MM=5,000-10,000 g/mol.

3) Fucoidan from Kraeber GmbH (Germany): on request, LMWF, 8,500 g/mol, HMWF, 600,000 g/mol, from different brown algae.

Example 1

Amination of the Hydroxyl Group of a Fucoidan

The fucoidan (500 mg, 1 mmole of 5 kDa) is dissolved in 15 mL of water and mixed with 5 mL 2.5 M NaOH and 0.1 mL of epichlorohydrin (1.3 mmoles). The mixture is stirred at 40° C. for 2 h and dialyzed against water at 25° C. for 2 days. After lyophilizing the dialysate, the residue is dissolved in 3 mL of 30% (v/v) ammonia in water and aminated at 40° C. for 90 min. The reaction mixture is dialyzed against water and lyophilized to give an aminated fucoidan.

According to said protocol, the quantity of primary amines depends on the quantity of epichlorohydrin which is introduced in the reaction. For a minimal quantity of epichlorohydrin, which may correspond to 0.1 mL of epichlorohydrin, the average number of primary amines which is introduced ranges from 1 to 10 primary amines per chain of fucoidan.

The reaction can be described as follows:

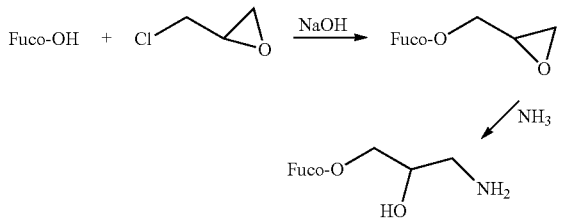

wherein Fuco means fucoidan.

However, the main drawback of said reaction is that it is not possible to precisely control where the substitution will occur within the chain, as said reaction may occur on any one of the hydroxyl (—OH) functions born by the fucoidan, in particular the fucose.

Thus, said method is not suitable for targeting the reducing end of the said fucoidan.

Example 2

Building the Bipolar Molecule or System Using a Two-Step Strategy

The main chemical step is the coupling of the fucoidan reducing end with primary amine bearing molecules i.e. lysine, oligolysine, or lysine mimetics and the reduction of the imine into secondary amine as widely described within basic organic chemistry books. Depending on the type of aminated molecules (i.e. DAP and DETA-fuco), two different strategies are illustrated herein.

Strategy 1:

In a first step, Fucoidan (F) is linked to diaminopropane ($NH_2$—$(CH_2)_3$—$NH_2$), leading to F—NH—$(CH_2)_3$—$NH_2$ (namely F—$NH_2$). Thus, said aminofucoidan is defined as a DAP-fuco.

In a strengthened glass tube, dissolve 500 mg of dried fucoidan in 5.4 mL of 1.5 M diaminopropane solution in bidistilled water. The tube is closed and heated for 3 h at 90° C. After cooling, 1.4 mL of freshly prepared dimethylborane 3 M in glacial acetic acid are added, and the mixture is heated for 3 h at 90° C.

The solution is neutralized, dialyzed (5×1 L with NaCl 1 M in 45 mM carbonate buffer pH 9.6; 5×1 L with NaCl M in water/ethanol 80/20 (v:v); 5×1 L in bidistilled water; in a dialysis chamber with a cut-off of 3000 Da and freeze-dried. F—$NH_2$ is obtained as a fluffy white solid in a 60% yield (w/w).

Thereafter, lysine, oligolysine (2-4 lysines), epsilon-aminocaproic acid or tranexamic acid, which will be referred herein as "amino acid derivatives", are optionally linked to F—$NH_2$ in a second step, as shown below.

To a solution of 5 mL of 10.4 mM amino acid derivative in bi-distilled water are successively added 20 mg of EDC and 12 mg of NHS, at room temperature. The mixture is kept under stirring for 15 min before addition of 76.4 mg of F—$NH_2$.

After 2 h under stirring at room temperature, the solution is dialyzed (5×1 L with NaCl 1 M in 45 mM carbonate buffer pH 9.6; 5×1 L with NaCl 0.5 M in water/ethanol 80/20 (v:v); 5×1 L in bidistilled water; cut-off 3000 D) and freeze-dried.)

Strategy 2:

Fucoidan (F) is straightly linked to diethylènetriamine (DETA=$NH_2$—$(CH_2)_2$—NH—$(CH_2)_2$—$NH_2$), as shown below. Thus, the aminofucoidan which is synthesized is defined as a DETA-fuco.

In a strengthened glass tube, dissolve 500 mg of dried fucoidan in 5.4 mL of 1.5 M DETA solution in bidistilled water. The tube is closed and heated for 3 h at 90° C. After cooling, 1.4 mL of freshly prepared dimethylborane 3 M in glacial acetic acid are added, and the mixture is heated for 3 h at 90° C.

The solution is neutralized and dialyzed (5×1 L with NaCl 1 M in 45 mM carbonate buffer pH 9.6; 5×1 L with NaCl 0.5 M in water/ethanol 80/20 (v:v); 5×1 L in bidistilled water; cut-off 3000 D) and freeze-dried).

Thereafter, lysine, oligolysine (2-4 lysines), epsilon-aminocaproic acid or tranexamic acid are linked to F—$NH_2$, as shown in strategy 1.

To a solution of 5 mL of 10.4 mM amino acid derivative in bi-distilled water are successively added 20 mg of EDC and 12 mg of NHS, at room temperature. The mixture is kept under stirring for 15 min before addition of 76.4 mg of F—$NH_2$.

After 2 h under stirring at room temperature, the solution is dialyzed (5×1 L with NaCl 1 M in 45 mM carbonate buffer pH 9.6; 5×1 L with NaCl 0.5 M in water/ethanol 80/20 (v:v); 5×1 L in bidistilled water; cut-off 3000 D) and freeze-dried.)

Conclusion:

Several amines and amino-acid derivatives have been obtained and tested, such as for instance, fuco-diaminopropane (DAP-fuco), fuco-diethylene triamine (DETA-fuco), fuco-tranexamique acid (tran-fuco), fuco-mono/polylysine (Lys-fuco, diLys-fuco, triLys-fuco . . . ).

Example 3

Physico-Chemical Properties of Fucoidans and Aminofucoidans.

A. Material & Methods.

Amination Quantification

The amount of primary amine was determined with phthalaldehyde colorimetric assay using bromopropylamine as the standard following Roth's work (M. Roth, 1971 "Fluorescence reaction for amino acids." *Analytical Chemistry*, 43, 880-882).

Fucose Quantification

Fucose quantification has been determined according to Dische (Z. Dische, 1955, New color reactions for determination of sugars in polysaccharides. *Methods Biochem. Anal.* 313-358).

Glucuronic Acid Quantification

Glucuronic acid quantification has been determined according to Bitter & Muir (T. Bitter et H. M. Muir, 1962, A modified uronic acid carbazole reaction. *Anal. Biochem.* 4 330-334).

Sulfate Quantification

Sulfate quantification can be determined according to the protocols described in Bachelet et al (Bachelet et al, 2009, Affinity of low molecular weight fucoidan for P-selectin triggers its binding to activated human platelets. Biochim Biophys Acta., 1790(2) 141-146), adapted from Gustafsson (L. Gustafsson, 1960, Determination of ultramicro amounts of sulphate as methylene blue-II: The reduction, Talanta 4, 236).

Sulfates are reduced as hydrogen sulphides using hydroiodic and hypophosphorous acids in acetic acid solution; then they are complexed by $Zn^{2+}$, and let to react with an aromatic diamine. Formation of methylene blue is quantified with absorption at 670 and 744 nm.

Molecular Mass Analysis

Molecular mass analysis can be determined using MALLS technique (Multi Angle Laser Light Scattering). Briefly, a gel filtration chromatography column (GMPWx1 from TSKgel), equilibrated in Tris buffer 10 mM, pH 7.4, NaCl 150 mM, 0.02% Sodium azide) is loaded at 0.5 mL/min. (HPLC pump Dionex Ultimate 3000). Signal is further detected using a refractive index detector (Iota2, Precison Instrument) and a light scattering detector (TREOS, Wyatt).

Infrared (IR) Spectrum Analysis

An IR spectrum is recorded using Fourier transform infrared-spectroscopy on a Nicolet avatar apparatus, using the Omnic (Nicolet) program suite. The sample is prepared in potassium bromide (KBr) in the range of 2% in weight of lyophilized product, and recorded with 32 scans. The spectrum of KBr alone is also recorded in similar conditions and automatically subtracted.

NMR-$^1$H Analysis

A $^1$H spectrum is recorded on a NMR Bruker 500 Avance III (probe: 5 mm PAQXI 1H/X) in D20 solvent (99.9%) after 3 lyophilisations: TD 32 k; 16 scans; SW: 10 ppm/500 Hz; P90°: 9.5 µs; Temperature 300 K; D1: 1 s.

B. Results

The physico-chemical properties of a set of fucoidans and aminofucoidans according to the invention have been measured and summarized in the table below:

|  | Amination ($NH_2$/mol PS) | Fucose (g/100 g) | Acide glucuronique (g/100 g) | Sulfate (g/100 g) | MW (*) (g/mol) |
|---|---|---|---|---|---|
| Fucoidan | — | 30.2 ± 4.1 | 19.5 ± 5.2 | 17.8 ± 2.4 | 5000 |
| Fucoidan-DAP | 1.05 ± 0.01 | 49.3 ± 4.6 | 25.6 ± 2.1 | 25.9 ± 3.8 | 10000 |
| Fucoidan-DAP-aminocaproïc acid | 0.32 ± 0.01 | 35.7 ± 13.2 | 8.2 ± 1.0 | 32 ± 2.1 | 10000 |
| Fucoïdan-DAP-tranexamic acid | 0.61 ± 0.02 | 34.9 ± 11.8 | 7.9 ± 1.8 | 30.6 ± 3.4 | 10000 |
| Fucoïdan-DETA | 1.08 ± 0.04 | 34.1 ± 13.3 | 13.8 ± 1.3 | 32.3 ± 1.1 | 10000 |
| Fucoïdan-DAP-lysine | 1.11 ± 0.03 | 31.2 ± 7.2 | 14.7 ± 1.9 | 30.2 ± 4.4 | 10000 |
| Fucoïdan-DAP-dilysine | 1.97 ± 0.04 | 53.4 ± 6.6 | 22.1 ± 1.9 | 18.6 ± 0.8 | 10000 |
| Fucoïdan-DAP-trilysine | 2.45 ± 0.01 | 45.4 ± 4.1 | 33.9 ± 3.5 | 21.5 ± 0.8 | 10000 |
| Fucoïdan-DAP-tétralysine | 2.38 ± 0.03 | 43.6 ± 4.6 | 20.7 ± 6.6 | 13.6 ± 0.7 | 10000 |

PS = polysaccharide
(*) = weightaveraged molecular weight (more or less 10%)

Each Analysis has been Repeated Three to Eight Times.

IR spectrums of fucoidan-DAP and fuco-DAP-dilysine/trilysine/tetralysine compounds highlight superposable spectrums which correspond to a sulfated polysaccharide, comprising a characteristic sulfate peak at 1200 $cm^{-1}$. The lack of significant differences between the DAP-aminated and the Lysine-aminated fucoidan demonstrates that coupling conditions between oligolysines (di-, tri- and tetralysines) do not alter the structure of said fucoidan. A vibrating band at 1540 $cm^{-1}$ is characteristic of an amide bond (CO—NH) between the polysaccharide and the oligolysines, and the lysines themselves.

As a complement to IR spectroscopy, NMR profiles of aminofucoidans and corresponding fucoidan preparations confirm that fucoidan structures are conserved after amination.

Example 4

In Vitro Pharmacological Evaluation of the Molecular Constructions.

A. Material & Methods

Clot Formation and Ex Vivo Fibrinolysis

Human platelet-rich and -poor plasma (PRP and PPP) were obtained from citrated blood after two centrifugation steps: at 120 g for 15 minutes followed by a second centrifugation step at 1200 g for 12 min. PRP was adjusted to 3×10$^8$ platelets per mL with poor platelet plasma (PPP) and supplemented with 75 µg/mL of fluorescein isothiocyanate-fibrinogen. Clot formation was induced by adding 10 mmol/L $CaCl_2$ in glass tubes and incubated for 1 hour at 37° C. After retraction, clots were washed in Hank's buffer (Sigma), rapidly dried on an absorbent paper and weighed. To assess fibrinolysis, PRP or PPP clots were incubated in Hanks' buffer containing the vectorized t-PA complexes (corresponding to 10 UI of t-PA, or 1.72 µg/mL) for 1 h at room temperature. Clots were transferred in a new eppendorf containing 500 µl of Hank's buffer supplemented with 1 µM of human plasminogen. The kinetic of fibrinolysis was evaluated by measuring the release of fluorescence from the clot to the supernatant with a spectrofluorimeter (485/520 nm). After 17 hours clots were reweighed to calculate the weigh loss corresponding to a total fibrinolysis.

Aminofucoidans tested in this experiment have been prepared according to strategy 1 (Tranexamic-fuco, dilysine- and trilysine-fucos) and strategy 2 (DETA-fuco), as described in example 2.

Aminofucoidans were used in variables molecular ratio to t-PA (10 UI (corresponding to 1.72 µg/ml): the 1/10 ratio was used for mono-amine fucoidans and 1/5 for poly-amine fucoidans. Evaluation criteria were the initial lysis kinetic (appearance of fluorescence in supernatant) and the final thrombus weight loss at 17H/37° C. incubation.

Aminofucoidan Vectorized t-PA

The single chain recombinant t-PA (American diagnostica) complex with aminofucoidans was formed by mixing 1 mole of t-PA with 10 moles of aminofucoidans in phosphate buffered saline supplemented with human serum albumin (HSA) 0.1% and 0.01% of Tween 20 for 2 hours at 4° C. and immediately used for clot lysis or stored at −80° C. for a future use. Other preparations have been made by addition of increasing amounts of aminofucoidans, up to 10 moles.

Single-chain recombinant t-PA is the secretion product of chinese Hamster Ovary cell line, which had been transfected with the cDNA for human t-PA obtained from a human melanoma cell line (Product No 173 from American diagnostic).

Characteristics of the preparation of single-chain recombinant t-PA:
  the molecular weight is about 70 000 Dalton,
  the purity is >98%,
  specific activity is approximately 580 000 UI/mg.

50 µg of this lyophilized t-PA carrier-free protein standard was reconstituted with 100 µl of 0.22 µm filtered deionized water and diluted to a 10 µg/ml solution in phosphate buffered saline.

The lysis kinetic experiments have been carried out as described in Jones et al. (Jones C I, Payne D A, Hayes P D, Naylor A R, Bell P R, Thomson M M, Goodall A H. The antithrombotic effect of dextran-40 in man is due to enhanced fibrinolysis in vivo. J Vasc Surg. 2008; 48:715-722).

Measurement of thrombus weight has been carried out as described in Boulaftali et al. (Boulaftali Y, Ho Tin Noe B, Pena A, Loyau S, Venisse L, Francois D, Richard B, Arocas V, Collet J P, Jandrot-Perrus M, Bouton M C. PLatelet Protease Nexin-1, a Serpin that Strongly Influences Fibrinolysis and Thrombolysis. Circulation. 2011; 123:1326-1334).

Thromboelastography experiments have been carried out on a rotative thromboelastograph (Rotem®) as described in Boulaftali et al. (Boulaftali Y, Ho Tin Noe B, Pena A, Loyau S, Venisse L, Francois D, Richard B, Arocas V, Collet J P, Jandrot-Perrus M, Bouton M C. PLatelet Protease Nexin-1, a Serpin that Strongly Influences Fibrinolysis and Thrombolysis. Circulation. 2011; 123:1326-1334) and Mallet et al. (Mallet S V, Cox D J A. Thromboelastograph Analysis. British J of anaest. 1992; 69:307-313).

B. Results

In a first step, since fucoidan binds to P-selectin expressed on activated and aggregated platelets, we evaluated in vitro the ability of the different aminofucoidans to bind to platelet-rich and platelet-poor thrombi using fluorescent fibrinogen (75 µg of Fg-FITC/ml plasma).

First, t-PA alone was more active on initial and final lysis of platelet-poor thrombus than on platelet-rich thrombus, demonstrating the antifibrinolytic activities of platelets.

Therefore there was no difference between t-PA alone and t-PA vectorized by aminofucoidan on lysis of platelet-poor thrombi including the thrombi weight loss at 17H, which is already maximal with t-PA alone (97%). In contrast, vectorized t-PA with aminofucoidan was able to significantly increase the initial lysis of platelet-rich thrombi as compared to t-PA alone (+50%, p<0.01). Among the tested aminofucoidans, Tranexamic-fuco, DAP-fuco and dilysine-fuco, were the most efficient to increase the initial rate of platelet-rich thrombus lysis.

Figure 1:
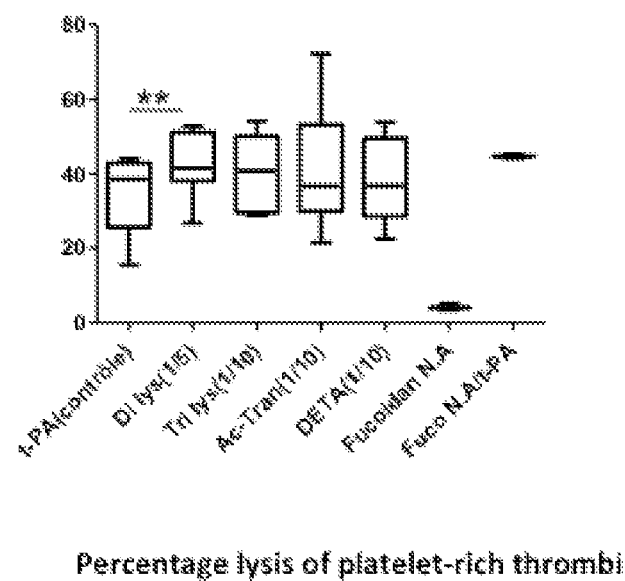
FIG. 1: In vitro lysis of a platelet-rich thrombus by aminofucoidan vectorized t-PA.

In parallel, aminofucoidans and vectorized t-PA also increased the loss of platelet-rich thrombus weight as compared to t-PA alone, 65% versus 30% respectively (p<0.01) (FIG. 1). Dilysine-fucoidan was among the most efficient.

In a third series of in vitro experiments, the ability of aminofucoidans to accelerate the lysis of a thrombus performed in total blood, including Red Blood Cells, has been tested with rotative thromboelastography (Rotem®). In this experiment dilysine-fucoidan vectorized t-PA, in a ratio (t-PA/fuco) of 1/5 or 1/10 increased the thrombus lysis to 75% as compared to t-PA alone (55%). In this experiment, the plasma PAI-1 was present.

Conclusion:

These tests are not able to evaluate the ability of aminofucoidans to vectorize the t-PA to thrombus in vivo, since in in vitro systems, amino-fucoidans target by diffusion only, and in the absence of PAI-1 (except for thromboelastograph experiments). However these in vitro pharmacological experiments demonstrate that amino-fucoidans do not significantly limit the accessibility of t-PA to thrombus (two last columns on the right). Moreover they show that amino-fucoidans as vectors for t-PA significantly facilitate thrombus lysis by t-PA in vitro, and that this effect is dependent on the presence of activated/aggregated platelets.

Example 5

In Vivo Validation of t-PA Vectorization by Amino-Fucoidans: Real-time Intravital Imaging of Thrombus Formation and Thrombolysis.

A. Material & Methods

DiLysine-fucoidan tested in this experiment has been prepared according to strategy 1 as described in example 2.

The group has recently published the ability of intravital microscopy to follow the lysis of thrombus in vivo. Thus, validation of t-PA vectorization by amino-fucoidans with intravital microscopy has been carried out according to the protocols described in Boulaftali et al. (Boulaftali et al., 2011, Platelet protease nexin-1, a serpin that strongly influences fibrinolysis and thrombolysis. Circulation; Boulaftali et al., 2012, The mouse dorsal skinfold chamber as a model for the study of thrombolysis by intravital microscopy. Thromb Haemost).

The thrombus is induced by local application of iron oxide on exposed vessels in mice. Fluorescent t-PA or a mixture of amino-fucoidans and t-PA are intravenously injected after iron oxide local application The fluorescence of t-PA and thrombus lysis were followed by intravital transillumination of the mesenteric tissue.

More precisely, after anesthesia (100 mg/kg ketamine, 10 mg/kg xylazine) and laparotomy, mouse mesenteric vessels were exposed for induction of thrombosis and video-microscopic intravital observation. Vascular injury was induced by placing a filter paper strip (1×0.5 mm) saturated with 10% FeCl3 (Sigma, St. Louis, Mo.) for 2 min 30. The filter paper was then removed, the exposed area was rinsed with saline, and thrombus formation following injury was examined in real-time by monitoring the accumulation of rhodamine 6 G-labeled platelets and leukocytes (3 mg rhodamine 6 G/kg mouse, Sigma, St. Louis, Mo.) and of Alexa 647 human-conjugated fibrinogen (10 mg/kg mouse, Invitrogen Life Technologies, Paisley, UK) using a fluorescence microscope (Axio Observer, Carl Zeiss MicroImaging) with a 5× objective connected to a CCD camera (Hamamatsu). All fluorescent markers were administered intravenously into the retro-orbital sinus prior to the induction of vascular injury. Platelet deposition and thrombus growth were monitored for 15 minutes following injury and fluorescent t-PA±DiLysine-fucoidan was then injected intravenously to thrombolysis of the partially occlusive-formed thrombi. Thrombus evolution was then examined in real-time for at least 1 hour following treatment.

B. Results

At 1 hour following FeCl3-induced injury (~45 min following treatment), occlusive thrombosis of injured vessels had occurred in all 3 mice treated with fluorescent t-PA alone. In contrast, vessel perfusion was maintained in all mice treated with t-PA combined with DiLysine-fucoidan. Furthermore, in these mice, a reduction in thrombus size was observed following treatment (FIG. 2).

Conclusion:

in vivo experiments demonstrate the beneficial effect of amino-fucoidans as vectors on thrombi lysis. In particular, these experiments show that amino-fucoidans potentiate the in vivo thrombolytic activity of peripherally injected t-PA.

The invention claimed is:

1. A vector that binds tissue plasminogen activator (t-PA) comprising a fucoidan moiety which is aminated by a covalent linkage between the reducing end of the said fucoidan moiety and a chemical group comprising one or more amino groups; with the proviso that the vector is not a fucoidan moiety as defined in formula (IV'):

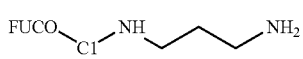

wherein
"FUCO" means a fucoidan moiety optionally containing one or more primary amine groups covalently linked to the fucoidan chain, and
C1 is the carbon atom at position 1 of the saccharide unit located at the reducing end of the fucoidan moiety.

2. The vector according to the previous claim, wherein said vector is a compound of formula (I):

FUCO-C1-[NH]$_y$-[L]$_z$-[NH]$_x$-R1  (I), wherein
"FUCO" means a fucoidan moiety, optionally containing one or more primary amine groups covalently linked to the fucoidan chain, x, y and z are independently selected from the integers 0 and 1, C1 is the carbon atom at position 1 of the saccharide unit located at the reducing end of the fucoidan moiety, L is a linker, and R1 is a chemical group comprising one or more amino groups, or consisting in one amino group, L and R1 are selected independently and may be the same or different.

3. The vector according to claim 2, wherein said vector is a compound of formula (I) wherein:

R1 is a chemical group comprising a primary-amine ended, linear or branched hydrocarbon chain; an aminoacid; a polyaminoacid; and/or a chemical group selected from the group consisting of: lysine, polylysine, arginine, polyarginine, ornithine, polyornithine, γ-aminobutyric acid, polyamines, polyetheramines, and a chemical group comprising a guanidine group or a primary amine, wherein:

said chemical group is optionally interrupted by one or more non aromatic hydrocarbon ring(s) having 5 or 6 carbon atoms, said chemical group is optionally interrupted by one or more heteroatoms, said chemical group optionally contains one or more amide groups and/or one or more ester groups, said chemical group is optionally substituted by one or more amine groups, said chemical group is optionally interrupted and/or substituted by one or more group(s), which are identical or different, and which are selected from the group consisting of: (a) a linear or branched hydrocarbon chain, (b) an aminoacid or a polyaminoacid (c) a polyamine or a polyetheramine, (d) a γ-aminobutyric acid (e) a guanidine group and (f) a primary amine.

4. The vector according to claim 1, wherein said fucoidan further comprises primary amine containing groups covalently linked to the fucoidan chain.

5. The vector according to claim 2, wherein R1 or L is substituted by 1 to 4 amine groups.

6. The vector according to claim 2, wherein [NH]x-R1 is of formula (VI) or (VII):

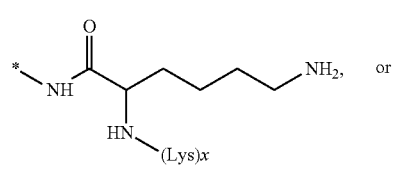

(VI)

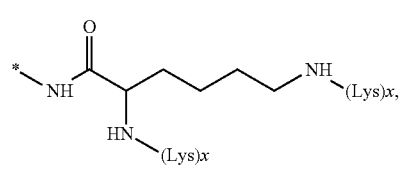

(VII)

wherein

«Lys» is a lysine or a lysine derivative, x is at least equal or superior to 1.

7. The vector according to claim 1, wherein said vector is selected from the group consisting of:

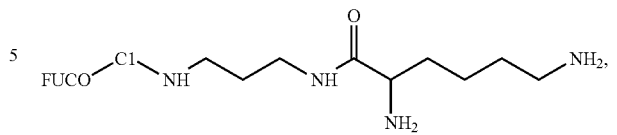

(II')

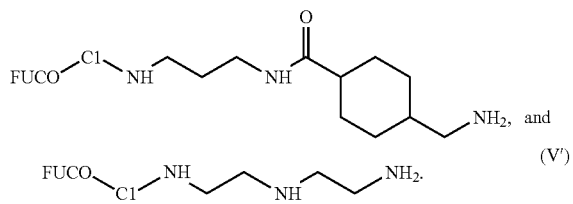

(III')

(V')

8. The vector according to claim 1, wherein the fucoidan moiety has an average molecular weight which is lower than 100 000 Da.

9. The vector according to claim 1, wherein the fucoidan moiety has an average molecular weight ranging from 2000 Da to 15 000 Da.

10. The vector according to claim 1, wherein the fucoidan moiety is polysulfated.

11. A vectorized t-PA comprising complexes of (i) tissue plasminogen activator (t-PA) with (ii) a vector that binds t-PA comprising a fucoidan moiety which is aminated by a covalent linkage between the reducing end of the said fucoidan moiety and a chemical group comprising one or more amino groups.

12. The vectorized t-PA according to claim 11, having a molar ratio of vector to t-PA ranging from 40:1 to 1:1.

13. A method for preventing or treating a thrombus in a subject comprising administering to said subject, as an active ingredient, a vectorized tissue plasminogen activator (t-PA) as defined in claim 11; or a vector that binds t-PA comprising a fucoidan moiety which is aminated by a covalent linkage between the reducing end of the said fucoidan moiety and a chemical group comprising one or more amino groups.

14. A method for preparing a vectorized t-PA comprising the steps of:

a) providing a vector that binds t-PA comprising a fucoidan moiety which is aminated by a covalent linkage between the reducing end of the said fucoidan moiety and a chemical group comprising one or more amino groups, b) providing t-PA, and c) bringing into contact the vector provided at step a) with the t-PA provided at step b), so as to obtain complexes between the said vector and t-PA.

15. A kit comprising:

a first container comprising a vector that binds t-PA comprising a fucoidan moiety which is aminated by a covalent linkage between the reducing end of the said fucoidan moiety and a chemical group comprising one or more amino groups, and a second container comprising t-PA.

16. A container comprising a vector that binds t-PA comprising a fucoidan moiety which is aminated by a covalent linkage between the reducing end of the said fucoidan moiety and a chemical group comprising one or more amino groups, and t-PA, wherein said vector and said t-PA are in an anhydrous form.

17. A pharmaceutical composition comprising complexes of (i) tissue plasminogen activator (t-PA) with (ii) a vector that binds t-PA comprising a fucoidan moiety which is aminated by a covalent linkage between the reducing end of the said fucoidan moiety and a chemical group comprising one or more amino groups.

18. A pharmaceutical composition for parenteral administration, comprising a vector that binds tissue plasminogen activator (t-PA) comprising a fucoidan moiety which is aminated by a covalent linkage between the reducing end of the said fucoidan moiety and a chemical group comprising one or more amino groups.

19. The vector according to claim 2, wherein R1 is a chemical group selected from the group consisting of: a lysine, a polylysine, and a lysine derivative.

* * * * *